(12) United States Patent
Ruoslahti et al.

(10) Patent No.: US 8,188,220 B2
(45) Date of Patent: May 29, 2012

(54) METHODS AND COMPOSITIONS RELATED TO TARGETING WOUNDS, REGENERATING TISSUE, AND TUMORS

(75) Inventors: Erkki Ruoslahti, LaJolla, CA (US); Tero Jarvinen, LaJolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 223 days.

(21) Appl. No.: 11/951,819

(22) Filed: Dec. 6, 2007

(65) Prior Publication Data

US 2009/0036349 A1    Feb. 5, 2009

Related U.S. Application Data

(60) Provisional application No. 60/868,772, filed on Dec. 6, 2006.

(51) Int. Cl.
*C07K 16/00* (2006.01)
(52) U.S. Cl. ........ 530/328; 530/329; 530/324; 530/300; 530/350
(58) Field of Classification Search .................. None
See application file for complete search history.

(56) References Cited

U.S. PATENT DOCUMENTS

| | | | |
|---|---|---|---|
| 4,418,052 A | 11/1983 | Wong | |
| 5,011,686 A | 4/1991 | Pang | |
| 5,024,829 A | 6/1991 | Berger et al. | |
| 5,789,542 A | 8/1998 | McLaughlin et al. | |
| 6,074,832 A * | 6/2000 | Venta et al. | 435/6 |
| 6,863,889 B2 * | 3/2005 | Shimkets et al. | 424/139.1 |
| 7,214,786 B2 * | 5/2007 | Kovalic et al. | 536/23.6 |
| 7,368,531 B2 * | 5/2008 | Rosen et al. | 530/350 |
| 7,745,391 B2 * | 6/2010 | Mintz et al. | 514/19.3 |
| 7,803,769 B2 * | 9/2010 | Sullivan et al. | 514/17.4 |
| 2004/0009122 A1 | 1/2004 | Klaveness et al. | |
| 2004/0031072 A1* | 2/2004 | La Rosa et al. | 800/278 |
| 2008/0213377 A1* | 9/2008 | Bhatia et al. | 424/489 |

FOREIGN PATENT DOCUMENTS

| | | |
|---|---|---|
| EP | 45665 | 2/1982 |
| WO | WO 01/55210 | * 8/2001 |
| WO | WO 03/101284 | * 12/2003 |

OTHER PUBLICATIONS

Harper's Review of Biochemistry eds. Martin et al, 20th ed. Lange Medical Publications (1985), p. 16.*
Abrahmsen L et al., Engineering subtilisin and its substrates for efficient ligation of peptide bonds in aqueous solution. Biochemistry 30:4151 (1991).
Allam et al. Cholera toxin triggers apoptosis in human lung cancer cell lines. Cancer Res 57: 2615-2618 (1997).
Allen et al. The Cambridge Crystallographic Data Centre: computer-based search, retrieval, analysis and display of information. Acta Crystallogr Section B, 35: 2331 (1979).
Almquist et al. Synthesis and biological activity of a ketomethylene analogue of a tripeptide inhibitor of angiotensin converting enzyme. J Med Chem 23: 1392-1398 (1980).
Altschul, S. F.,et al. "Gapped BLAST and PSI-BLAST: a new generation of protein database search programs." Nucleic Acids Res 25:3389-3402 (1997).
Alvarez-Bravo et al. Novel synthetic antimicrobial peptides effective against methicillin-resistant *Staphylococcus aureus*. Biochem J 302: 535-538 (1994).
Anthony-Cahill et al., Site-specific mutagenesis with unnatural amino acids. TIBS, 14:400-403 (1989).
Arap, W.,et al. "Cancer treatment by targeted drug delivery to tumor vasculature in a mouse model." Science 279:377-380 (1998).
Arap, W.et al. "Targeting the prostate for destruction through a vascular address." Proc Natl Acad Sci U S A 99:1527-1531 (2002).
Ashcroft et al., "Mice lacking Smad3 show accelerated wound healing and an impaired local inflammatory response," Nat. Cell Biol., 1, 260-266 (1999).
Baggiolini M, et al. Interleukin-8, a chemotactic and inflammatory cytokine. FEBS Lett. 307: 97-101 (1992).
Benner, Expanding the genetic lexicon: incorporating non-standard amino acids into proteins by ribosome-based synthesis. TIB Tech, 12, 158-163 (1994).
Bessalle et al. All-D-magainin: chirality, antimicrobial activity and proteolytic resistance. FEBS 274: 151-155 (1990).
Blondelle and Houghten, Design of model amphipathic peptides having potent antimicrobial activities. Biochem 31: 12688-12694, (1992).
Border et al., "Natural inhibitor of transforming growth factor-beta protects against scarring in experimental kidney disease," Nature, 360, 361-364 (1992).
Border et al., "Suppression of experimental glomerulonephritis by antiserum against transforming growth factor beta 1," Nature, 346, 371-374 (1990).
Borgstrom et al. Importance of VEGF for breast cancer angiogenesis in vivo: implications from intravital microscopy of combination treatments with an anti-VEGF neutralizing monoclonal antibody and doxorubicin. Anticancer Res 19: 4203-4214 (1999).
Brunner et al., "Extracellular regulation of TGF-beta activity in wound repair: growth factor latency as a sensor mechanism for injury," Thromb. Haemost., 92, 253-261 (2004).
Chan, et al. Prospective randomized trial of docetaxel versus doxorubicin in patients with metastatic breast cancer. J Clin Oncol 17: 2341-2354 (1999). Chargé SBP, Rudnicki MA. "Cellular and molecular regulation of muscle regeneration." Physiol Rev. 84:209-238 (2004).
Chen Y, et al. "Matrix contraction by dermal fibroblasts requires transforming growth factor-/activin-linked kinase 5, heparan sulfate-containing proteoglycans, and MEK/ERK: insights into pathological scarring in chronic fibrotic disease." Am J Pathol, 167:1699-1711 (2005).

(Continued)

Primary Examiner — Sheela J Huff
(74) Attorney, Agent, or Firm — Pabst Patent Group LLP

(57) ABSTRACT

Disclosed are compositions and methods useful for targeting regenerating tissue, wounds, and tumors. The compositions and methods are based on peptide sequences that selectively bind to and home to regenerating tissue, wound sites, and tumors in animals. The disclosed targeting is useful for delivering therapeutic and detectable agents to regenerating tissue, wound sites, and tumors in animals.

74 Claims, 10 Drawing Sheets

OTHER PUBLICATIONS

Cheon SS, et al., "Beta-catenin regulates wound size and mediates the effect of TGF-beta in cutaneous healing," Faseb J., 20, 692-701 (2006).

Clark-Lewis I, et al. Chemical synthesis, purification, and characterization of two inflammatory proteins, neutrophil activating peptide 1 (interleukin-8) and neutrophil activating peptide. Biochemistry 30: 3128 (1991).

Clark-Lewis I, et al. Structural requirements for interleukin-8 function identified by design of analogs and CXC chemokine hybrids. J. Biol. Chem. 269: 16075 (1994).

Creighton, Proteins: Structures and Molecular Properties WH Freeman, New York (1984).

Crown J, The platinum agents: A role in breast cancer treatment? Seminars in Oncol 28: 28-37 (2001).

Davies et al., "Decorin suppresses neurocan, brevican, phosphacan and NG2 expression and promotes axon growth across adult rat spinal cord injuries," Eur J. Neurosci, 19, 1226-1242 (2004).

Davis et al. Isolation of angiopoietin-1, a ligand for the TIE2 receptor, by secretion-trap expression cloning. Cell 87: 1161-1169 (1996).

Dawson et al., Synthesis of Proteins by Native Chemical Ligation, Science, 266, 776-779 (1994).

deLisle Milton RC, et al. Techniques in Protein Chemistry IV. Academic Press, New York pp. 257-267 (1992).

Desmouliere et al., "Tissue repair, contraction, and the myofibroblast," Wound Repair Regen., 13, 7-12 (2005).

Dyson M, et al. Comparison of the effects of moist and dry conditions on the process of angiogenesis during dermal repair. J Invest Dermatol. 99:729-733, 1992.

Esko JD, Stewart TE, Taylor WH. "Animal cell mutants defective in glycosaminoglycan biosynthesis." Proc Natl Acad Sci U S A. 82(10):3197-201 (May 1985).

Falanga, "Wound healing and its impairment in the diapetic foot," Lancet, 366, 1736-1743 (2006).

Fisher et al. Tamoxifen for prevention of breast cancer: report of the National Surgical Adjuvant Breast and Bowel Project P-1 Study. J Natl Cancer Inst 90: 1371-1388 (1998).

Fitzpatrick and Garnett, Design, synthesis and in vitro testing of methotrexate carrier conjugates linked via oligopeptide spacers. Anticancer Drug Des 10: 1-9 (1995).

Folkman and Shing, Angiogenesis. J Biol Chem 267: 10931-10934 (1992).

Folkman, Addressing tumor blood vessels. Nature Biotechnology 15: 510 (1997).

Folkman, "Angiogenesis," Annu Rev Med, 57, 1-18 (2006).

Fukushima et al, "The use of an antifibrosis agent to improve muscle recovery after laceration," Am J. Sports Med., 29, 394-402 (2001).

Galang, C.K., et al. "Changes in the expression of many Ets family transcription factors and of potential target genes in normal mammary tissue and tumors." J.Biol. Chem. 279:11281-11292 (2004).

Gerlag et al., "Suppression of murine collagen-induced arthritis by targeted apoptosis of synovial neovasculature," Arthritis Research, 3, 357-361 (2001).

Goodman et al., Peptidomimetics for Drug Design, "Burger's Medicinal Chemistry and Drug Discovery", vol. 1 (ed. M. E. Wolff; John Wiley & Sons) 803-861 (1995).

Gorvy DA, et al. "Experimental manipulation of transforming growth factor—isoforms significantly affects adhesion formation in a murine surgical model." Am J Pathol 167:1005-1019 (2005).

Grotendorst et al., "Individual domains of connective tissue growth factor regulate fibroblast proliferation and myofibroblast differentiation," FASEB J., 19, 729-38 (2005).

Grotendorst Gr, Rahmanie H, Duncan MR. "Combinatorial signaling pathways determine fibroblast proliferation and myofibroblast differentiation." FASEB J. 18:469-79 (2004).

Hagedorn and Bikfalvi, Target molecules for anti-angiogenic therapy: from basic research to clinical trials. Crit Rev Oncol Hematol 34: 89-110 (2000).

Hann, Chem. Soc Perkin Trans. I, On the double bond isostere of the peptide bond: preparation of an enkephalin analogue, p. 307-314 (1982).

Harris et al., Cancer: Principles and practice of oncology, (1997) Part 1.

Harris et al., Cancer: Principles and practice of oncology, (1997) Part 2.

Hildebrand et al., "Interaction of the small interstitial proteoglycans biglycan, decorin and fibromodulin with transforming growth factor β," Biochem J, 302 (Pt 2), 527-534 (1994).

Hoffman et al., "Progressive vascular changes in a transgenic mouse model of squamous cell carcinoma," Cancer Cell, 4, 383-91 (2003).

Holladay et al. Synthesis of hydroxyethylene and ketomethylene dipeptide isosteres. Tetrahedron Lett. 24:4401-4404 (1983).

Homandberg et al. Heparin-binding fragments of fibronectin are potent inhibitors of endothelial cell growth: structure-function correlations. Biochim Biophys Acta 874: 61-71 (1986).

Homandberg et al. Heparin-binding fragments of fibronectin are potent inhibitors of endothelial cell growth. Am J Pathe 120: 327-332 (1985).

Hruby. Conformational restrictions of biologically active peptides via amino acid side chain groups. Life Sci. 31: 189-199 (1982).

Hu Q, Ueno N, Behringer RR. "Restriction of BMP4 activity domains in the developing neural tube of the mouse embryo." EMBO Rep 5:734-739 (2004).

Hudson D, et al. Methionine enkephalin and isosteric analogues. I. Synthesis on a phenolic resin support. Int J Pept Prot Res 14: 177-185 (1979).

Ibba et al., Towards engineering proteins by site-directed incorporation in vivo of non-natural amino acids., Biotechnology, 12, 678-682 (1994).

Ibba, Strategies for in vitro and in vivo translation with nonnatural amino acids. Biotechnology & Genetic Engineering Reviews, 13, 197-216 (1995).

International Preliminary Report on Patentability and Written Opinion of PCT/US2007/086627 dated Jun. 18, 2009.

International Search Report for PCT/US2007/086627 dated Dec. 8, 2008.

Iozzo et al., "Decorin is a biological ligand for the epidermal growth factor receptor," J Biol Chem, 274(8), 4489-4492 (1999).

Jarvelainen H, et al., "A role for decorin in cutaneous wound healing and angiogenesis," Wound Repair Regen., 14, 443-452 (2006).

Javadpour et al. De novo antimicrobial peptides with low mammalian cell toxicity. J Med Chem 39: 3107-3113 (1996).

Jennings-White et al. Synthesis of ketomethylene analogs of dipeptides. Tetrahedron Lett 23: 2533 (1982).

Joliot A. "Transduction peptides within naturally occurring proteins." Sci STRE 313:pe54 (2005).

Joyce et al., "Stage-specific vascular markers revealed by phage display in a mouse model of pancreatic islet tumorigenesis," Cancer Cell, 4, 393-403 (2003).

Järvinen M. Healing of a crush injury in rat striated muscle. 3. A microangiographical study of the effect of early mobilization and immobilization on capillary ingrowth. Acta Pathol Microbiol Scand. 84A:85-94, 1976.

Kirsch et al. Anti-angiogenic treatment strategies for malignant brain tumors. J Neurooncol 50: 149-163 (2000).

Kolonin et al., "Synchronous selection of homing peptides for multiple tissues by in vivo phage display," FASEB J., 20, 979-81 (2006).

Kreitman and Pastan, Recombinant toxins containing human granulocyte-macrophage colony-stimulating factor and either pseudomonas exotoxin or diphtheria toxin kill gastrointestinal cancer and leukemia cells. Blood 90: 252-259 (1997).

Kreuger, J., Spillman, D. and Lindahl, Ulf. "Interactions between heparan sulfate and proteins: the concept of specificity." J. Cell Biol. 174: 323-327 (2006).

Krusius et al., "Primary structure of an extracellular matrix proteoglycan core protein deduced from cloned cDNA," Proc. Natl. Acad. Sci. USA, 83, 7683-7 (1986).

Laakkonen et al., "A tumor-homing peptide with a targeting specificity related to lymphatic vessels," Nat Med, 8, 751-755 (2002).

Laakkonen, P., Akerman, M.E., Biliran, H., Yang, M., Ferrer, F., Karpanen, T., Hoffman, R.M., and Ruoslahti, E. "Antitumor activity of a homing peptide that targets tumor lymphatics and tumor cells." Proc. Natl. Acad. Sci. USA. 101:9381-9386 (2004).

Laemmli, U. K. "Cleavage of structural proteins during the assembly of the head of bacteriophage T4." Nature 227:680-685 (1970).

Leask et al., "All in the CCN family: essential matricellular signaling modulators emerge from the bunker," J. Cell. Sci., 119, 4803-4810 (2006).
Leask et al., "TGF-beta signaling and the fibrotic response," Faseb J., 18, 816-827 (2004).
Liu et al., "In vivo interrogation of the molecular display of atherosclerotic lesion surfaces," Am. J. Path., 163, 1859-71 (2003).
Lyon M, Rushton G, Gallagher JT. "The interaction of the transforming growth factor-s with heparin/heparan sulfate is isoform-specific." J Biol Chem 272(29):18000-6 (1997).
Maloy and Kari, Structure-activity studies on magainins and other host defense peptides. Biopolymers 37: 105-122 (1995).
Mancheno et al. A peptide of nine amino acid residues from alpha-sarcin cytotoxin is a membrane-perturbing structure. J Pept Res 51: 142-148 (1998).
Martin, "Wound-healing-aiming for perfect skin regeneration," Science, 276, 75-81 (1997).
Martin, et al. Cancer gene therapy by thyroid hormone-mediated expression of toxin genes. Cancer Res 60: 3218-3224 (2000).
O'Reilly et al. Angiostatin: a novel angiogenesis inhibitor that mediates the suppression of metastases by a Lewis lung carcinoma. Cell 79: 315-328 (1994).
O'Reilly et al. Antiangiogenic activity of the cleaved conformation of the serpin antithrombin. Science 285: 1926-1928 (1999).
O'Reilly et al. Endostatin: an endogenous inhibitor of angiogenesis and tumor growth. Cell 88: 277-285 (1997).
Ohkawara B, Iemura S, ten Dijke P, Ueno N "Action range of BMP is defined by its N-terminal basic amino acid core." Curr Biol 12: 205-209 (2002).
Osborne and Coronado-Heinsohn, Targeting the epidermal growth factor receptor in breast cancer cell lines with a recombinant ligand fusion toxin (DAB389EGF). Cancer J Sci Am 2: 175 (1996).
Paavonen et al. Vascular endothelial growth factor receptor-3 in lymphangiogenesis in wound healing. Am J Pathol., 156(5):1499-504 (2000).
Paridaens et al. Paclitaxel versus doxorubicin as first-line single-agent chemotherapy for metastatic breast cancer: a European Organization for Research and Treatment of Cancer Randomized Study with cross-over. J Clin Oncol 18: 724 (2000).
Pasqualini, R., and Ruoslahti, E. "Organ targeting in vivo using phage display peptide libraries." Nature 380:364-366 (1996).
Pilch J, Brown DM, Komatsu M, Järvinen TAH, Yang M, Peters D, Hoffman RM, Ruoslahti E: "Peptides selected for clotted plasma accumulate in tumor stroma and wounds." Proc. Natl. Acad. Sci USA 103:2800-2803 (2006).
Porkka et al., "A fragment of the HMGN2 protein homes to the nuclei of tumor cells and tumor endothelial cells in vivo," Proc Natl Acad Sci U S A, 99, 7444-7449 (2002).
Powers et al. Indium-111 platelet scintigraphy in cerebrovascular disease. Neurology 32: 938 (1982).
Rajarathnam K, et al. 1H NMR studies of interleukin 8 analogs: characterization of the domains essential for function. Biochemistry 33: 6623-30 (1994).
Rajotte et al., "Molecular heterogeneity of the vascular endothelium revealed by in vivo phage display," J Clin Invest, 102, 430-437 (1998).
Rajotte, D., and Ruoslahti, E. "Membrane dipeptidase is the receptor for a lung-targeting peptide identified by in vivo phage display." J Biol Chem 274:11593-11598 (1999).
Reed CC, Waterhouse A, Kirby S, Kay P, Owens RT, McQuillan DJ, Iozzo RV. "Decorin prevents metastatic spreading of breast cancer." Oncogene 24:1104-10 (2005).
Reed et al., "The role of decorin in collagen fibrillogenesis and skin homeostasis," Glycoconj. J., 19, 249-255 (2002).
Rider CC. "Heparin/heparan sulphate binding in the TGF-cytokine superfamily." Biochem Soc Trans 34:458-460 (2006).
Rizo et al., Constrained peptides: models of bioactive peptides and protein substructures. Ann. Rev. Biochem., 61, 387 (1992).
Ruoslahti E, Yamaguchi Y. "Proteoglycans as modulators of growth factor activities." Cell 64: 867-9 (1991).
Ruoslahti, "Specialization of tumour vasculature," Nat Rev Cancer, 2, 83-90 (2002).

Rusinko et al. Using CONCORD to Construct a Large Database of Three-Dimensional Coordinates from Connection Tables. J Chem Inf Comput Sci 29: 251 (1989).
Saberwal et al. Cell-lytic and antibacterial peptides that act by perturbing the barrier function of membranes: facets of their conformational features, structure-function correlations and membrane-perturbing abilities. Biochim Biophys Acta 1197: 109-131 (1994).
Santra et al., "An anti-oncogenic role for decorin. Down-regulation of ErbB2 leads to growth suppression and cytodifferentiation of mammary carcinoma cells," J. Biol. Chem., 275, 35153-35161 (2000).
Santra M, Reed CC, Iozzo RV. "Decorin binds to a narrow region of the epidermal growth factor (EGF) receptor, partially overlapping but distinct from the EGF-binding epitope." J Biol Chem 277:35671-81 (2002).
Schnolzer M, et al. Constructing proteins by dovetailing unprotected synthetic peptides: backbone-engineered HIV protease. Science 256: 221 (1992).
Seidler DG, et al., "Decorin protein core inhibits in vivo cancer growth and metabolism by hindering epidermal growth factor receptor function and triggering apoptosis via caspase-3 activation," J Biol Chem, 281, 26408-26418 (2006).
Shah et al., "Neutralisation of TGF-beta 1 and TGF-beta 2 or exogenous addition of TGF-beta 3 to cutaneous rat wounds reduces scarring," J Cell Sci., 108, 985-1002 (1995).
Shipitsin M, et al., "Molecular definition of breast tumor heterogeneity," Cancer Cell, 11, 259-273 (2007).
Singer et al., "Cutaneous wound healing," N Engl J Med, 341, 738-746 (1999).
Slavin J. Fibroblast growth factors: at the heart of angiogenesis. Cell Biol Int 19: 431-444 (1995).
Spatola AF in Chemistry and Biochemistry of Amino Acids, Peptides, and Proteins, B. Weinstein, eds., Marcel Dekker, New York, p. 267-357 (1983).
Spatola et al. Structure-activity relationships of enkephalins containing serially replaced thiomethylene amide bond surrogates. Life Scie 38: 1243-1249 (1986).
Steiner, In "Angiogenesis: Key principles-Science, technology and medicine" pp. 449-454 (eds. Steiner et al.; Birkhauser Verlag, 1992).
Stewart, et al., "Cancer: Principles and practice of oncology", 5th ed., chap. 19, p. 452-467 (1997).
Sullivan MM, et al. "Matricellular hevin regulates decorin production and collagen assembly." J Biol Chem 281: 27621-27632 (2006).
Suri et al. Requisite role of angiopoietin-1, a ligand for the TIE2 receptor, during embryonic angiogenesis. Cell 87: 1171-1180 (1996).
Thakur ML et al. Indium-LLL labeled platelets: studies on preparation and evaluation of in vitro and in vivo functions. Throm Res 9:345 (1976).
Thorson et al., A biosynthetic approach for the incorporation of unnatural amino acids into proteins. Methods in Molec. Biol., 77, 43-73 (1991).
Tralhao JG, et al. "In vivo selective and distant killing of cancer cells using adenovirus-mediated decorin gene transfer." FASEB J 17:464-6 (2003).
Weis SM, et al., "A role for decorin in the remodeling of myocardial infarction," Matrix Biol., 24, 313-324 (2005).
Werner et al., "Regulation of wound healing by growth factors and cytokines," Physiol Rev, 83, 835-870 (2003).
White et al., Antibody targeted immunotherapy for treatment of Malignancy. Annu. Rev. Med., 52, 125-141 (2001).
Yamaguchi et al., "Expression of human proteoglycan in Chinese hamster ovary cells inhibits cell proliferation," Nature, 336, 244-246 (1988).
Yamaguchi et al., "Negative regulation of transforming growth factor-β by the proteoglycan decorin," Nature, 346, 281-284 (1990).
Yang et al., "Active transforming growth factor-beta in wound repair: determination using a new assay," Am. J. Pathol., 154, 105-111 (1999).
Zhang et al., "Decorin regulates assembly of collagen fibrils and acquisition of biomechanical properties during tendon development," J. Cell Biochem., 98, 1436-1449 (2006).

Zhang L, et al. Lymphatic zip codes in premalignant lesions and tumors. Cancer Res. 66:5696-5706, 2006.

Zoller. New recombinant DNA methodology for protein engineering. Current Opin. In Biotech. 3: 348-354 (1992).

Zorko M, Langel U. "Cell penetrating peptides: mechanism and kinetics of cargo delivery." Adv. Drug Deliv Rev 57:529-45 (2005).

Zurita et al. Combinatorial screenings in patients: the interleukin-11 receptor alpha as a candidate target in the progression of human prostate cancer, Cancer Res. 64:435-9 (2004).

* cited by examiner

METHODS AND COMPOSITIONS RELATED TO TARGETING WOUNDS, REGENERATING TISSUE, AND TUMORS

CROSS-REFERENCE TO RELATED APPLICATIONS

This application claims benefit of U.S. Provisional Application No. 60/868,772, filed Dec. 6, 2006, herein incorporated by reference in its entirety.

STATEMENT REGARDING FEDERALLY SPONSORED RESEARCH

This invention was made with government support under grants PO1 CA 82713 and CA 30199 from the National Cancer Institute of the NIH, and grant DAMD17-02-1-0315 from the DOD. The government has certain rights in the invention

FIELD OF THE INVENTION

The present invention relates generally to the fields of molecular medicine, more specifically, to molecules that selectively home to wound sites and regenerating tissue.

BACKGROUND OF THE INVENTION

Tissue regeneration, inflammation and tumors induce the growth of new blood vessels from pre-existing ones. This process, angiogenesis, is a vital requirement for wound healing as the formation of new blood vessels allows a variety of mediators, nutrients, and oxygen to reach the healing tissue (Martin 1997, Singer & Clark 1999, Falanga 2006, Folkman 2006). Newly formed blood vessels differ in structure from pre-existing vasculature. Such differences have been extensively characterized by comparing tumor vasculature to normal vessels (Ruoslahti, 2002). Angiogenic vessels in non-malignant tissues and in pre-malignant lesions share markers with tumor vessels (Gerlag et al, 2001), but distinct markers also exist (Hoffman et al., 2003; Joyce et al., 2003).

Regarding tissue injuries, substantive basic science and clinical research have been conducted to evaluate the mechanisms of wound healing, the efficacy of various modalities for treatment of wounds, and the best methods for diagnosing wound infection. Tissue injuries caused by trauma, medical procedures, and inflammation are a major medical problem. Systemic medication is available for most major medical conditions, but therapeutic options in promoting tissue regeneration are largely limited to local intervention. As deep injuries and multiple sites of injury often limit the usefulness of local treatment, systemic approaches to tissue regeneration are valuable.

A major problem limiting tissue regeneration is scar formation. The response to tissue injury in adult mammals seems to be mainly focused on quick sealing on the injury. Fibroblast (astrocyte, smooth muscle cell) proliferation and enhanced extracellular matrix production are the main element of the scar formation, and the scar prevents tissue regeneration. In contrast, fetal tissues heal by a process that restores the original tissue architecture with no scarring. Transforming growth factor β (TGF-β) is a major factor responsible for impaired tissue regeneration, scar formation and fibrosis (Werner and Grose 2002; Brunner and Blakytny 2004; Leask and Abraham 2004).

A major hurdle to advances in treating cancer is the relative lack of agents that can selectively target the cancer while sparing normal tissue. For example, radiation therapy and surgery, which generally are localized treatments, can cause substantial damage to normal tissue in the treatment field, resulting in scarring and loss of normal tissue. Chemotherapy, in comparison, which generally is administered systemically, can cause substantial damage to organs such as the bone marrow, mucosae, skin and small intestine, which undergo rapid cell turnover and continuous cell division. As a result, undesirable side effects such as nausea, loss of hair and drop in blood cell count often occur when a cancer patient is treated intravenously with a chemotherapeutic drug. Such undesirable side effects can limit the amount of a drug that can be safely administered, thereby hampering survival rate and impacting the quality of patient life.

Thus, there is a need for new therapeutic strategies for selectively targeting regenerating tissue as well as wounds, and reducing the side effects associated with systemic therapy. The present invention satisfies this need by providing molecules that selectively home to regenerating tissue and tumors, and which are suitable for selectively targeting drugs, gene therapy vectors or other agents to the appropriate tissue. Related advantages also are provided.

BRIEF SUMMARY OF THE INVENTION

Disclosed herein are isolated peptides comprising an amino acid segment comprising the amino acid sequence of SEQ ID NO: 1 or SEQ ID NO: 2, or the amino acid sequence of SEQ ID NO: 1 or SEQ ID NO: 2 having one or more conservative amino acid substitutions. The isolated peptide can have a length of less than 100, 50, or 20 residues. Also, the amino acid segment can be cyclic, and can be cyclicized via a disulfide bond. The isolated peptide can consist of the amino acid segment.

The peptides disclosed herein can selectively home to regenerating tissue. Regenerating tissue can include that found at a site of injury, a surgical site, or a tumor. The peptide can also home to a site of inflammation, or arthritis.

Also disclosed herein are conjugates, wherein the conjugate comprises a moiety linked to a peptide as disclosed herein. The peptide can selectively interact with regenerating tissue, or with tissue at a site of inflammation, or with tissue at a site of arthritis. The peptide can also selectively interact with a tumor. The moiety can be an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination. The moiety can be a therapeutic agent, a detectable agent, a virus, or a phage.

Also disclosed herein are methods of directing a moiety to regenerating tissue, comprising administering to a subject a conjugate, as disclosed herein. Disclosed are methods wherein the therapeutic effect comprises a reduction in inflammation, an increase in speed of wound healing, a reduction in the amount of scar tissue, decrease in pain, decrease in swelling, or decrease in necrosis.

Also disclosed are methods of directing a moiety to tumors, comprising administering to a subject a conjugate as disclosed herein. The conjugate can have a therapeutic effect, and the subject can have one or more sites to be targeted, wherein the moiety is directed to one or more of the sites to be targeted. The subject can have cancer, wherein the moiety is directed to tumor angiogenesis in the subject. The conjugate can have a therapeutic effect on the cancer, such as reducing the size or growth of a tumor. The moiety can also be used to detect the cancer, visualize one or more tumors, or both.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
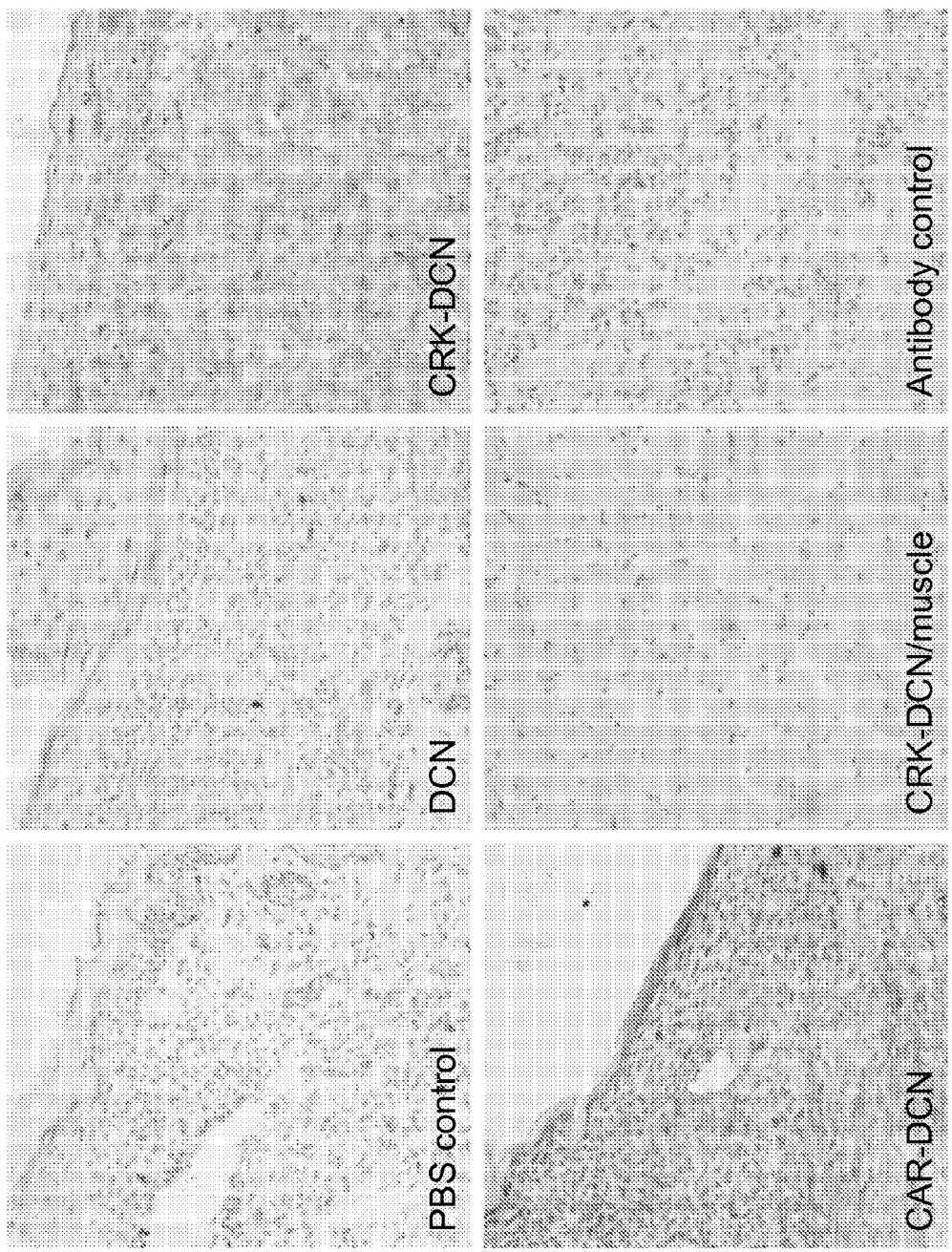
FIG. 1 shows the accumulation of homing peptide-guided decorins in wound tissue. Mice with full thickness skin wounds, received daily intravenous injections as indicated on Days 3-5 after the wounding (n=4 per group, 2 wounds per animal). On Day 5, the presence of decorins was evaluated with anti-6-histidine tag antibody (which stains brown) by examining two sections from each wound. The wounds of mice injected with non-modified decorin (DCN) were weakly positive for decorin staining, whereas strong staining was observed in CRK-decorin and CAR-decorin wounds. No decorin-staining was observed in skeletal muscle underlying the skin wounds of mice treated with DCN, CAR-DCN or CRK-DCN (shown for CRK-DCN; CRK-DCN/muscle). No staining was seen in wound tissue when class-matched mouse IgG was substituted for the anti-6-histidine tag antibody (Antibody control).

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. GENERAL

In vivo screening of phage-displayed peptide libraries was used to probe vascular specialization. This method has revealed a large degree of heterogeneity in the vasculature; and tissue-specific homing peptides have been identified for a large number of normal organs and tissues (Rajotte at al., 1998; Zhang et al., 2005; Kolonin et al., 2006), and tumors and atherosclerotic lesions have been shown to carry their own vascular markers, both in the blood vessels and in lymphatics (Ruoslahti, 2002; Liu et al., 2003; Zhang et al., 2006). It was reasoned that surveying non-malignant angiogenesis could reveal a different repertoire of markers than has been gleaned from studies with tumor. Wounds were chosen as the target, as wounds are one of the few the locations where angiogenesis takes place in an adult organism.

Two peptides that selectively target phage to skin and tendon wounds were identified: CARSKNKDC(CAR, SEQ ID NO: 1) and CRKDKC(CRK, SEQ ID NO: 2). CAR displays homology to heparin-binding sites in various proteins, and binds to cell surface heparan sulfate and heparin. CRK is homologous to a segment in thrombospondin type 1 repeat. Intravenously injected CAR and CRK phage, and the fluorescein-labeled free peptides selectively accumulate at wound sites, partially co-localizing with blood vessels. The CAR peptide shows a preference for early stages of wound healing, whereas the CRK favors wounds at later stages of wound healing. The CAR peptide is internalized into the target cells and delivers the fluorescent label into their nuclei. These results show that the molecular markers in the vasculature of wound tissues change as healing progresses. The peptides recognizing these markers can be useful, for example, in delivering treatments into regenerating tissues.

These peptides can deliver a payload to wound tissue with a 20 to 100-fold selectivity. These peptides appear to be different from previously described tumor-homing peptides, and they reveal changes in the molecular profile of wound vasculature as the wound heals.

These wound-homing peptides were used to demonstrate the feasibility of systemic targeting of wounds to promote wound healing and tissue regeneration. The peptides were used as a specific homing element for targeted delivery of decorin into skin wounds. Decorin is a small leucine-rich chondroitin sulfate proteoglycan. It is a multifunctional protein that regulates collagen fibril formation, acts as a natural antagonist of TGF-β (Yamaguchi and Ruoslahti, 1989), and has other regulatory functions as well. Decorin prevents tissue fibrosis (Border et al., 1992), promoting tissue regeneration. Peptide-decorin fusion proteins were designed, and then used to treat mice with skin wounds. The fusion proteins were strikingly effective in preventing scar formation, where an equivalent dose of decorin was inactive. The targeting approach can make systemic enhancement of tissue regeneration a feasible option. These results identify new therapy options for surgical wounds as well as for various kinds of internal trauma that goes beyond approaches based on the direct, topical application of therapeutic molecules at the wound site.

B. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed are methods and compositions related to an isolated peptide comprising an amino acid segment comprising the amino acid sequence of SEQ ID NO: 1 or SEQ ID NO: 2 or related amino acid sequences.

Also disclosed are isolated peptides comprising an amino acid segment comprising, for example, the amino acid sequence of SEQ ID NO: 1 or SEQ ID NO: 2, or the amino acid sequence of SEQ ID NO:1 or SEQ ID NO:2 having one or more conservative amino acid substitutions. For example, the peptide can have 1, 2, 3, 4, or 5 conservative amino acid substitutions. One of skill in the art is readily able to assess which amino acids can be substituted and retain the function of the peptide.

Also disclosed are conjugates, wherein the conjugate comprises a moiety linked to a peptide comprising an amino acid segment comprising, for example, the amino acid sequence of SEQ ID NO: 1 or SEQ ID NO: 2, or the amino acid sequence of SEQ ID NO:1 or SEQ ID NO:2 having one or more conservative amino acid substitutions.

The peptide can have a length of less than 100 residues. The peptide can have a length of less than 50 residues. The peptide can have a length of less than 20 residues. The amino acid segment can comprise the amino acid sequence of SEQ ID NO:1 or SEQ ID NO:2. The amino acid sequence of SEQ ID NO:1 or SEQ ID NO:2 can have one or more conservative amino acid substitutions. The amino acid segment can be circular or cyclic. The amino acid segment can be circularized or cyclized via a disulfide bond. The peptide can consist of the amino acid segment. The peptide can selectively home to regenerating tissue, wound sites, or tumors. The peptide can selectively interact with regenerating tissue, wound sites, or tumors.

The moiety can be a moiety is a an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination. The moiety can be a therapeutic agent. The moiety can be a detectable agent. The conjugate can comprises a virus. The conjugate can comprise a phage. The conjugate can further comprise a second peptide, wherein the second peptide comprising an amino acid segment comprising the amino acid sequence of SEQ ID NO: 1 or SEQ ID NO: 2, or the amino acid sequence of SEQ ID NO:1 or SEQ ID NO:2 having one or more conservative amino acid substitutions.

The subject can have regenerating tissue, such as that found in a wound. The wound can be chronic, or can be acute. The wound can be in any stage of healing, from the inflammatory stage, to granulation, to contraction, to epithelialization, to the remodeling phase, which includes collagenation and the formation of scar tissue. The wound can be from an auto, boat, or airplane accident, a gunshot, stabbing or knife accident, a fall, an industrial accident, or impalement. The wound can also be formed during surgery, for example. The wound can also be the result of a treatment, such as the implanting of a port.

The conjugate can treat at least one of the sites of injury. The conjugate can have a therapeutic effect on at least one of the sites of injury. The moiety can be used to detect, visualize, or image at least one of the sites of injury, or a combination. When a tumor is being treated, the moiety is directed to angiogenic tissue in the subject. The conjugate can treat the cancer. The conjugate can have a therapeutic effect on the cancer. The size of a tumor can be reduced. The growth of a tumor can be reduced, stopped or reversed. The moiety can be used to detect the cancer, visualize one or more tumors, or both.

A. Homing Molecules

Disclosed are homing molecules that selectively home to sites of injuries and wounds, regenerating tissue, and tumors. A variety of homing molecules can be used in the disclosed compositions, conjugates and methods. Such homing molecules include, without limitation, peptides as disclosed herein. The disclosed compounds, compositions, conjugates and methods can include or use the disclosed homing molecules in various forms, including peptides and peptidomimetics as disclosed. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby.

As used herein, the term "molecule" is used broadly to mean a polymeric or non-polymeric organic chemical such as a small molecule drug; a nucleic acid molecule such as an RNA, a DNA such as a cDNA or oligonucleotide; a peptide; or a protein such as a growth factor receptor or an antibody or fragment thereof such as an Fv, Fd, or Fab fragment or another antibody fragment containing the antigen-binding domain.

The term "homing molecule" as used herein, means any molecule that selectively homes in vivo to the clotted plasma of one or more wound tissue, regenerating tissue, or tumors in preference to normal tissue. Similarly, the term "homing peptide" or "homing peptidomimetic" means a peptide that selectively homes in vivo to regenerating tissue, wounds, or tumors in preference to normal tissue. It is understood that a homing molecule that selectively homes in vivo to regenerating tissue, wounds, or tumors or can exhibit preferential homing to regenerating tissue, wounds, or tumors.

By "selectively homes" is meant that, in vivo, the homing molecule binds preferentially to the target as compared to non-target. For example, the homing molecule can bind preferentially to regenerating tissue, wound tissue, or tumors, as compared to non-regenerating tissue, non-wound tissue, or non-tumors. Such a homing molecule can selectively home, for example, to regenerating tissue. Selective homing to, for example, regenerating tissue generally is characterized by at least a two-fold greater localization within regenerating tissue, as compared to several tissue types of non-regenerating tissue. A homing molecule can be characterized by 5-fold, 10-fold, 20-fold or more preferential localization to regenerating tissue as compared to several or many tissue types of non-regenerating tissue, or as compared to-most or all non-regenerating tissue. Thus, it is understood that, in some cases, a homing molecule homes, in part, to one or more normal organs in addition to homing to regenerating tissue, wound tissue, or tumors. Selective homing can also be referred to as targeting.

In some embodiments, a homing molecule can be a molecule that selectively homes regenerating tissue, wound tissue, or tumors and which is not an antibody or antigen-binding fragment thereof. The term "antibody" is an art-recognized term that refers to a peptide or polypeptide containing one or more complementarity determining regions (CDRs). See, for example, Borrabaeck, Antibody Engineering 2nd Edition, Oxford University Press, New York (1995).

Homing, including preferential and/or selective homing, does not mean that the homing molecule does not bind to any normal and/or non-targeted areas (for example, non-tumor, non-clot, and/or non-wound). In some embodiments, homing selectivity can be, for example, at least about 20-fold, at least about 30-fold, at least about 50-fold, at least about 75-fold, at least about 100-fold, at least about 150-fold, or at least about 200-fold selective for a corresponding target in terms of relative $K_i$ over other non-target components. In some embodiments, the homing molecule can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, in some preferred embodiments, the homing molecule can have a $K_i$ value against a target of less than about 200 nM, less than about 150 nM, less than about 100 nM, or less than about 75 nM. In some preferred embodiments, the homing molecule can have a $K_i$ value against a target of more than about 50 nM, more than about 25 nM, more than about 20 nM, more than about 15 nM, more than about 10 nM, more than about 5 nM, more than about 3 nM, or more than about 1 nM. In some preferred embodiments, the targeting moiety binds its target with a $K_D$ less than about $10^{-8}$ M, less than about $10^{-9}$ M, less than about $10^{-10}$ M, less than about $10^{-11}$ M, less than about $10^{-12}$ M, less than about $10^{-13}$ M, or less than about $10^{-14}$ M.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces.

1. Peptides and Peptidomimetics

Disclosed are methods and compositions related to an isolated peptide comprising an amino acid segment comprising the amino acid sequence of SEQ ID NO: 1 or SEQ ID NO: 2 or related amino acid sequences. The isolated peptides can comprise, for example, an amino acid segment comprising, for example, the amino acid sequence of SEQ ID NO: 1 or SEQ ID NO: 2, or the amino acid sequence of SEQ ID NO:1 or SEQ ID NO:2 having one or more conservative amino acid substitutions.

The amino acid segment can comprise an amino acid sequence at least about 90%, 80%, 70%, or 60% identical to the amino acid sequence of SEQ ID NO: 1 or SEQ ID NO:2, or any percentage in between that represents a change, including addition or deletion, of one or more amino acid. The amino acid segment can comprise the amino acid sequence of SEQ ID NO:1 or SEQ ID NO:2. The amino acid segment can comprise the amino acid sequence of SEQ ID NO:1 or SEQ ID NO:2 having one, two, three, four, five, six, seven, eight, or nine conservative amino acid substitutions. The amino acid segment can comprise a chimera of the amino acid sequence SEQ ID NO:1 or SEQ ID NO:2. Such a chimera can be additive, where sequence of one sequence is added to another sequence, substitutional, where sequence of one sequence is substituted for sequence of another sequence, or a combination. The disclosed peptides can consist of the amino acid segment.

The amino acid segment can be linear, circular or cyclic. The amino acid segment can be circularized or cyclized via any suitable linkage, for example, a disulfide bond.

The peptide can have any suitable length, such as a length of less than 100 residues. The peptide can have a length of less than 50 residues. The peptide can have a length of less than 20 residues.

The disclosed peptides can selectively home to regenerating tissue, wound tissue, or tumors. The disclosed peptides can selectively interact with regenerating tissue, wound tissue, or tumors.

Also disclosed are isolated peptides which has a length of less than 100 residues and which includes the amino acid sequence CAR (SEQ ID NO: 1) or a peptidomimetic thereof, or CRK (SEQ ID NO: 2) or a peptidomimetic thereof. Such an isolated peptide can have, for example, a length of less than 50 residues or a length of less than 20 residues. In particular embodiments, disclosed can be a peptide that includes the amino acid sequence SEQ ID NO: 1 or SEQ ID NO: 2, and has a length of less than 20, 50 or 100 residues.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35 or 40 residues. The disclosed peptides also can be useful in the context of a significantly longer sequence. For example, as disclosed herein, the CAR and CRK peptides (SEQ ID NO: 1 and SEQ ID NO: 2, respectively) maintained the ability to home when fused to a phage coat protein, confirming that the disclosed peptides can have selective homing activity when embedded in a larger protein sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

i. Peptide Variants

As discussed herein there are numerous variants of the CAR and CRK peptides that are herein contemplated. In addition, to the known functional variants there are derivatives of the peptides which can also function in the disclosed methods and compositions. Protein and peptide variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues.

Deletions are characterized by the removal of one or more amino acid residues from the protein or peptide sequence. Typically, no more than about from 2 to 6 residues are deleted at any one site within the protein or peptide molecule. These variants can be prepared by site specific mutagenesis of nucleotides in the DNA encoding the protein or peptide, thereby producing DNA encoding the variant, and thereafter expressing the DNA in recombinant cell culture. Techniques for making substitution mutations at predetermined sites in DNA having a known sequence are well known. Amino acid substitutions are typically of single residues, but can occur at a number of different locations at once; insertions usually will be on the order of about from 1 to 10 amino acid residues; and deletions will range about from 1 to 10 residues. Deletions or insertions preferably are made in adjacent pairs, i.e. a deletion of 2 residues or insertion of 2 residues. Substitutions, deletions, insertions or any combination thereof can be combined to arrive at a final construct. The mutations generally should not place the sequence out of reading frame (unless a truncated peptide is intended) and preferably will not create complementary regions that could produce secondary mRNA structure. Substitutional variants are those in which at least one residue has been removed and a different residue inserted in its place.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of both CAR and CRK (SEQ ID NOs: 1 and 2) encompass sequences containing one, two, three, four or more amino acid substitutions relative to SEQ ID NO: 1 and 2, and that such variants can include naturally and non-naturally occurring amino acid analogs.

Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of CAR and SEQ ID NO: 2 sets forth a particular sequence of CRK. Specifically disclosed are variants of these and other proteins herein disclosed which have at least, 70% or 75% or 80% or 85% or 90% or 95% homology to the stated sequence, or any percentage in between that represents a change of amino acid, including a substitution, addition, or deletion. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent than those discussed above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10): 400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence SEQ ID NO: 1 or SEQ ID NO: 2, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides which contains a homing peptide fused to a second peptide having a separate function. Such bifunctional peptides have at least two functions conferred by different portions of the full-length molecule and can, for example, display anti-angiogenic activity or pro-apoptotic activity in addition to selective homing activity.

Also disclosed are isolated multivalent peptides that includes at least two subsequences each independently containing a homing molecule (for example, the amino acid sequence SEQ ID NO: 1 or 2, or a conservative variant or peptidomimetic thereof). The multivalent peptide can have, for example, at least three, at least five or at least ten of such subsequences each independently containing a homing molecule (for example, the amino acid sequence of SEQ ID NO: 1 or 2, or a conservative variant or peptidomimetic thereof). In particular embodiments, the multivalent peptide can have two, three, four, five, six, seven, eight, nine, ten, fifteen or twenty identical or non-identical subsequences. In a further embodiment, the multivalent peptide can contain identical subsequences, which consist of a homing molecule (for example, the amino acid sequence SEQ ID NO: 1 or 2, or a conservative variant or peptidomimetic thereof). In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$—$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—$C^\epsilon$ or $C^\alpha$—$C^\Delta$ cyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide, for example, with activity in selectively homing to tumor stroma, wounds, and plasma clots.

If desired, an isolated peptide, or a homing molecule as discussed further elsewhere herein, can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl) benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

B. Conjugates

Disclosed are conjugates comprising a moiety and a homing molecule, such as a peptide as disclosed herein. For example, disclosed are conjugates containing a therapeutic agent linked to a homing molecule that selectively homes to regenerating tissue, wound tissue, or tumors. Disclosed conjugates can comprise, for example, a moiety linked to a peptide comprising an amino acid segment comprising, for example, the amino acid sequence of SEQ ID NO: 1 or SEQ ID NO: 2, or the amino acid sequence of SEQ ID NO:1 or SEQ ID NO:2 having one or more conservative amino acid substitutions.

Any form or type of homing molecule as disclosed herein can be used in the disclosed conjugates. The moiety can be any molecule. Preferably the moiety is a molecule that is usefully targeted to the target of the homing molecule. For example, moieties that affect the target, such as moieties with therapeutic effect, or that facilitate detection, visualization or imaging of the target, such as fluorescent molecule or radionuclides. Disclosed peptides that home to regenerating tissue, wound tissue, or tumors can be usefully combined with, for example, moieties that can, for example, promote wound healing, treat inflammation or pain, or treat cancer. A variety of therapeutic agents are useful in the conjugates including, without limitation, a moiety that is an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination.

A conjugate containing multiple homing molecules can include, for example, two or more, three or more, five or more, ten or more, twenty or more, thirty or more, forty or more, fifty or more, 100 or more, 200 or more, 300 or more, 400 or more, 500 or more, or 1000 or more homing molecules. In one embodiment, the conjugate includes homing molecules that all have an identical amino acid sequence. In another embodiment, the conjugate includes homing molecules having two or more non-identical amino acid sequences. For example, SEQ ID NO: 1 and SEQ ID NO: 2 can be used separately or together. Moieties useful in a conjugate incorporating multiple homing molecules include, without limitation, phage, retroviruses, adenoviruses, adeno-associated viruses and other viruses, cells, liposomes, polymeric matrices, non-polymeric matrices, particles such as gold particles, microdevices, nanodevices, and nano-scale semiconductor materials.

A conjugate can contain, for example, a liposome or other polymeric matrix linked to at least two homing molecules. If desired, the liposome or other polymeric matrix can be linked to at least ten, at least 100 or at least 1000 homing molecules. Liposomes can be useful in such conjugates; liposomes consist of phospholipids or other lipids, are nontoxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule.

Components of the disclosed conjugates can be combined, linked and/or coupled in any suitable manner. For example, moieties and homing molecules can be associated covalently or non-covalently, directly or indirectly, with or without a linker moiety.

C. Moieties

Disclosed are compositions and methods of directing a moiety to a target. As used herein, the term "moiety" is used broadly to mean a physical, chemical, or biological material that generally imparts a biologically useful function to a linked molecule. A moiety can be any natural or nonnatural material including, without limitation, a biological material, such as a cell, phage or other virus; an organic chemical such as a small molecule; a radionuclide; nucleic acid molecule or oligonucleotide; a polypeptide; or a peptide. Useful moieties include, yet are not limited to an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination. Useful moieties further include, without limitation, phage and other viruses, cells, liposomes, polymeric matrices, non-polymeric matrices or particles such as gold particles, microdevices and nanodevices, and nano-scale semiconductor materials. These and other moieties known in the art can be components of a conjugate.

1. Therapeutic Agents

The moiety incorporated into a conjugate can be a therapeutic agent. As used herein, the term "therapeutic agent" means a molecule which has one or more biological activities in a normal or pathologic tissue. A variety of therapeutic agents can be included in a conjugate.

The conjugates disclosed herein can also be used to treat wounds or tissue injuries. Moieties useful for this purpose can include molecules belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue.

Examples of active agents include but are not limited to steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful for targeting a wound or other infected sites. Thus, also disclosed are conjugates in which a homing molecule that selectively homes to tumor stroma, wounds, or plasma clots and interacts with fibrin-fibronectin is linked to an antimicrobial peptide, where the conjugate is selectively internalized and exhibits a high toxicity to the targeted area, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. An antimicrobial peptide can have biological activity due to, for example, the ability to form ion channels through membrane bilayers as a consequence of self-aggregation.

Antimicrobial peptide can be highly basic and can have a linear or cyclic structure. As discussed further below, an antimicrobial peptide can have an amphipathic .alpha.-helical structure (see U.S. Pat. No. 5,789,542; Javadpour et al., J. Med. Chem. 39:3107-3113 (1996); and Blondelle and Houghten, Biochem. 31: 12688-12694 (1992)). An antimicrobial peptide also can be, for example, a β-strand/sheet-forming peptide as described in Mancheno et al., J. Peptide Res. 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:-151-155 (1990).); and Blondelle and Houghten in Bristol (Ed.), Annual Reports in Medicinal Chemistry pages 159-168 Academic Press, San Diego). An antimicrobial peptide also can be an analog of a natural peptide, especially one that retains or enhances amphipathicity (see below).

An antimicrobial peptide incorporated into a conjugate can have low mammalian cell toxicity when not linked to a tumor homing molecule. Mammalian cell toxicity readily can be assessed using routine assays. As an example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, disclosed are conjugates in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$, (SEQ ID NO: 19) for example, is an antimicrobial peptide which induces marked mitochondrial swelling at a concentration of 10 μM, significantly less than the concentration required to kill eukaryotic cells.

An antimicrobial peptide that induces significant mitochondrial swelling at, for example, 50 μM, 40 μM, 30 μM, 20 μM, 10 μM, or less, is considered a peptide that promotes disruption of mitochondrial membranes.

An antimicrobial peptide can include, for example, the sequence (KLAKLAK)$_2$ (SEQ ID NO: 20), (KLAKKLA)$_2$ (SEQ ID NO: 21), (KAAKKAA)$_2$ (SEQ ID NO: 22), or (KLGKKLG)$_3$ (SEQ ID NO: 23), and, in one embodiment, includes the sequence $_D$(KLAKLAK)$_2$ (SEQ ID NO: 19).

Antimicrobial peptides can have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, Proteins: Structures and Molecular Properties W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., Biochim. Biophys. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., Biochim. Biophys. Acta 1197: 109-131 (1994)). One skilled in the art understands that helix-promoting amino acids such as leucine and alanine can be advantageously included in an antimicrobial peptide (see, for example, Creighton, supra, 1984). Synthetic, antimicrobial peptides having an amphipathic α-helical structure are known in the art, for example, as described in U.S. Pat. No. 5,789,542 to McLaughlin and Becker.

It is understood by one skilled in the art of medicinal oncology that these and other agents are useful therapeutic agents, which can be used separately or together in the disclosed conjugates and methods. Thus, it is understood that a conjugate can contain one or more of such therapeutic agents and that additional components can be included as part of the conjugate, if desired. As a non-limiting example, it can be desirable in some cases to utilize an oligopeptide spacer between the homing molecule and the therapeutic agent (Fitzpatrick and Garnett, Anticancer Drug Des. 10:1-9 (1995)).

Other useful agents include thrombolytics, aspirin, anticoagulants, painkillers and tranquilizers, beta-blockers, ace-inhibitors, nitrates, rhythm-stabilizing drugs, and diuretics. The disclosed conjugates can use any of these or similar agents.

In some embodiments, a conjugate can contains a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an antimetabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in the conjugates. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

A cancer chemotherapeutic agent useful in a conjugate also can be an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, Nature Biotechnology 15:510 (1997); Steiner, In "Angiogenesis: Key principles-Science, technology and medicine," pp. 449-454 (eds. Steiner et al.; Birkhauser Verlag, 1992)), which can contribute to its effectiveness in treating cancer.

An alkylating agent such as melphalan or chlorambucil also can be a cancer chemotherapeutic agent useful in a conjugate. Similarly, a vinca alkaloid such as vindesine, vinblastine or vinorelbine; or an antimetabolite such as 5-fluorouracil, 5-fluorouridine or a derivative thereof can be a cancer chemotherapeutic agent useful in a conjugate.

A platinum agent also can be a cancer chemotherapeutic agent useful in the conjugates. Such a platinum agent can be, for example, cisplatin or carboplatin as described, for example, in Crown, Seminars in Oncol. 28:28-37 (2001). Other cancer chemotherapeutic agents useful in a conjugate include, without limitation, methotrexate, mitomycin-C, adriamycin, ifosfamide and ansamycins.

A cancer chemotherapeutic agent for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate for treatment of breast cancer (Fisher et al., J. Natl. Cancer Instit. 90:1371-1388 (1998)).

A therapeutic agent useful in a conjugate can be an antibody such as a humanized monoclonal antibody. As an example, the anti-epidermal growth factor receptor 2 (HER2) antibody, trastuzumab (Herceptin; Genentech, South San Francisco, Calif.) is a therapeutic agent useful in a conjugate for treating HER2/neu overexpressing breast cancers (White et al., Annu. Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas exotoxin* A, cholera toxin, ligand fusion toxins such as DAB389EGF, ricinus communis toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

In one embodiment, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferonα. (IFN-α); interferon .gamma. (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas exotoxin* A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent useful in a conjugate also can be an anti-angiogenic agent. As used herein, the term "anti-angiogenic agent" means a molecule that reduces or prevents angiogenesis, which is the growth and development of blood vessels. The conjugates can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Vascular endothelial growth factor (VEGF) has been shown to be important for angiogenesis in many types of cancer, including breast cancer angiogenesis in vivo (Borgstrom et al., Anticancer Res. 19:4213-4214 (1999)). The biological effects of VEGF include stimulation of endothelial cell proliferation, survival, migration and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., supra, 1999). An anti-angiogenic agent also can inhibit another angiogenic factor such as a member of the fibroblast growth factor family such as FGF-1 (acidic), FGF-2 (basic), FGF-4 or FGF-5 (Slavin et al., Cell Biol. Int. 19:431-444 (1995); Folkman and Shing, J. Biol. Chem. 267:10931-10934 (1992)) or an angiogenic factor such as angiopoietin-1, a factor that signals through the endothelial cell-specific Tie2 receptor tyrosine kinase (Davis et al., Cell 87:1161-1169 (1996); and Suri et al., Cell 87:1171-1180 (1996)), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of anti-thrombin; collagenase inhibitors; basement membrane turnover inhibitors; angiostatic steroids; platelet factor 4 and fragments and peptides thereof; thrombospondin and fragments and peptides thereof; and doxorubicin (O'Reilly et al., Cell 79:315-328 (1994)); O'Reilly et al., Cell 88:277-285 (1997); Homandberg et al., Am. J. Path. 120:327-332 (1985); Homandberg et-al., Biochim. Biophys. Acta 874:61-71 (1986); and O'Reilly et al., Science 285:1926-1928 (1999)). Commercially available anti-angiogenic agents include, for example, angiostatin, endostatin, metastatin and 2ME2 (EntreMed; Rockville, Md.); anti-VEGF antibodies such as Avastin (Genentech; South San Francisco, Calif.); and VEGFR-2 inhibitors such as SU5416, a small molecule inhibitor of VEGFR-2 (SUGEN; South San Francisco, Calif.) and SU6668 (SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

2. Detectable Agents

The moiety in the disclosed conjugates can also be a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed conjugates and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include moieties which emit or can be caused to emit detectable radiation (e.g., fluorescence excitation, radioactive decay, spin resonance excitation, etc.), moieties which affect local electromagnetic fields (e.g., magnetic, ferromagnetic, ferromagnetic, paramagnetic, and/or superparamagnetic species), moieties which absorb or scatter radiation energy (e.g., chromophores and/or fluorophores), quantum dots, heavy elements and/or compounds thereof. See, e.g., detectable agents described in U.S. Publication No. 2004/0009122. Other examples of detectable agents include a proton-emitting moiety, a radiopaque moiety, and/or a radioactive moiety, such as a radionuclide like Tc-99m and/or Xe-13. Such moieties can be used as a radiopharmaceutical. In still other embodiments, the disclosed compositions can comprise one or more different types of detectable agents, including any combination of the detectable agents disclosed herein.

Useful fluorescent moieties include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio. Fluorescent probes and there use are also described in Handbook of Fluorescent Probes and Research Products by Richard P. Haugland.

Further examples of radioactive detectable agents include gamma emitters, e.g., the gamma emitters In-111, I-125 and I-131, Rhenium-186 and 188, and Br-77 (see. e.g., Thakur, M. L. et al., Throm Res. Vol. 9 pg. 345 (1976); Powers et al., Neurology Vol. 32 pg. 938 (1982); and U.S. Pat. No. 5,011,686); positron emitters, such as Cu-64, C-11, and O-15, as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, I-123, Nd-147, Pm-151, Sm-153, Gd-159, Tb-161, Er-171 and/or Tl-201.

The use of Technitium-99m (Tc-99m) is preferable and has been described in other applications, for example, see U.S. Pat. No. 4,418,052 and U.S. Pat. No. 5,024,829. Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 4,7,10-tetraazacyclododecane-N-,N',N''',N'''-tetraacetic acid (DOTA) and/or metallothionein, any of which can be covalently attached to the targeting moiety. In some embodiments, an aqueous mixture of technetium-99m, a reducing agent, and a water-soluble ligand can be prepared and then allowed to react with a disclosed targeting moiety. Such methods are known in the art, see e.g., International Publication No. WO 99/64446. In some embodiments, compositions comprising radioactive iodine, can be prepared using an exchange reaction. For example, exchange of hot iodine for cold iodine is well known in the art. Alternatively, a radio-iodine labeled compound can be prepared from the corresponding bromo compound via a tributylstannyl intermediate.

Magnetic detectable agents include paramagnetic contrasting agents, e.g., gadolinium diethylenetriaminepentaacetic acid, e.g., used with magnetic resonance imaging (MRI) (see, e.g., De Roos, A. et al., Int. J. Card. Imaging Vol. 7 pg. 133 (1991)). Some preferred embodiments use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium(III), manganese(II), iron(II), iron(III), cobalt(II), nickel(II), copper(II), praseodymium(III), neodymium(III), samarium(III) and ytterbium(III), as well as gadolinium(III), terbium(III), dysoprosium(III), holmium(III), and erbium(III). Some preferred embodiments use atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In preferred embodiments, the detectable agent can be coupled to the homing molecule in such a way so as not to interfere with the ability of the homing molecule to home to the target. In some embodiments, the detectable agent can be chemically bound to the homing molecule. In some embodiments, the detectable agent can be chemically bound to a moiety that is itself chemically bound to the homing molecule, indirectly linking the imaging and targeting moieties.

D. Pharmaceutical Compositions and Carriers

The disclosed conjugates can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

1. Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

E. Combinatorial Chemistry

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NOS: 1 and 2 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, CAR and CRK, are also disclosed. Thus, the products produced using the combinatorial or screening approaches that involve the disclosed compositions, such as, CAR and CRK, are also considered herein disclosed.

F. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, CAR and CRK, are also disclosed. Thus, the products produced using the molecular modeling approaches that involve the disclosed compositions, such as, CAR and CRK are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annul. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

G. Compositions with Similar Functions

It is understood that the compositions disclosed herein have certain functions, such as interacting with the fibrin-fibronectin complex. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

H. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include CAR and CRK.

I. Mixtures

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

J. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

K. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Methods

Disclosed herein are methods of directing a moiety to regenerating tissue, comprising administering to the subject a conjugate as disclosed herein. As discussed above, the regenerating tissue can be at the site of a wound, such as those caused by injury or surgery. Since the peptides home to regenerating tissue, they can be used in any method associated with regenerating tissue. The conjugate can have a therapeutic effect on at least one of the wound sites. The moiety can be used to detect, visualize, or image at least one of the wound sites, or a combination.

Disclosed are methods wherein the therapeutic effect comprises a reduction in inflammation. By "reduction in inflammation" is meant a decrease in inflammation compared to if the inflammation were not treated. The reduction in inflammation can be about 5, 10, 15, 20, 25, 30, 35, 40, 45, 50, 55, 60, 65, 70, 75, 80, 85, 90, 95, or 100% increase, or about 1, 2, 3, 4, 5, 6, 7, 8, 9, 10, 20, 30, 40, 50, 60, 70, 80, 90, or 100 fold, or higher. There can also be an increase in speed of wound healing, as compared to an untreated wound. The increase in speed of wound healing can be about 5, 10, 15, 20, 25, 30, 35, 40, 45, 50, 55, 60, 65, 70, 75, 80, 85, 90, 95, or 100% increase, or about 1, 2, 3, 4, 5, 6, 7, 8, 9, 10, 20, 30, 40, 50, 60, 70, 80, 90, or 100 fold, or higher. There can also be a reduction in the amount of scar tissue as compared to an untreated site of injury or wound. The reduction in the amount of scar tissue can be about 5, 10, 15, 20, 25, 30, 35, 40, 45, 50, 55, 60, 65, 70, 75, 80, 85, 90, 95, or 100%. There can also be a reduction in the amount of pain experienced by the subject in need thereof, compared to the amount of pain experienced if not treated for pain. This reduction in pain can be about a 5, 10, 15, 20, 25, 30, 35, 40, 45, 50, 55, 60, 65, 70, 75, 80, 85, 90, 95, or 100% reduction. There can also be a decrease in swelling. This decrease in swelling can be compared to untreated swelling, and can be about a 5, 10, 15, 20, 25, 30, 35, 40, 45, 50, 55, 60, 65, 70, 75, 80, 85, 90, 95, or 100% decrease in swelling. There can also be a decrease in tissue necrosis, compared to untreated tissue. The decrease in necrosis can be about 5, 10, 15, 20, 25, 30, 35, 40, 45, 50, 55, 60, 65, 70, 75, 80, 85, 90, 95, or 100%.

The conjugates disclosed herein can also be useful in subjects with arthritis and other inflammatory diseases, as such lesions are often associated with angiogenesis. The conjugates can be used to treat or diagnose any disease, condition, or disorder associated with angiogenesis. For example, macular degeneration and diabetic vascular complications can be diagnosed and/or treated.

The conjugates disclosed herein can also be useful in subjects with tumors, since tumors are associated with angiogenesis. Disclosed is a method of directing a moiety to tumors, comprising administering to the subject the any of the conjugates disclosed herein. For example, the conjugate can have a therapeutic effect. The subject can have one or more sites to be targeted, wherein the moiety is directed to one or more of the sites to be targeted. For example, the subject can have multiple wounds or lesions that can be treated with the moieties disclosed herein. The subject can also have cancer, and the moiety can be directed to tumor angiogenesis in the subject. In this case, the conjugate can have a therapeutic effect on the cancer. For example, the size of the tumor can be reduced, or the growth of the tumor can be reduced, stopped, or reversed. The moiety can also be used to detect the cancer, visualize one or more tumors, or both.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

The compositions can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The compositions disclosed herein and the compositions necessary to perform the disclosed methods can be made using any method known to those of skill in the art for that particular reagent or compound unless otherwise specifically noted.

One method of producing the disclosed proteins, such as SEQ ID NOs: 1 and 2, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Molecular Changes in the Vasculature of Injured Tissues i. Identification of Homing Peptides by Phage Display To identify candidate peptides that home into the vasculature in healing wounds, phage libraries were screened in vivo. A T7-phage library (diversity $8.75 \times 10^8$) was intravenously injected into rats 5 days after wounding of the skin and tendons. The 5-day time point was chosen because the number of blood vessels in the healing wound peaks at that time (Järvinen 1976; Thompson 1991; Dyson 1992; Paavonen 2000). Separate screens for phage that home to tendon or skin wounds yielded phage pools with increased affinity for the target tissues. Sequencing of individual phage clones revealed 2 peptide sequences that appeared multiple times in the selected pools. These clones were chosen for further analysis.

One of the selected peptides is a cyclic peptide CARSKNKDC (referred to as CAR, SEQ ID NO: 3). This peptide was obtained from the tendon screens. BLAST analysis (Altschul et al. 1997) showed that the CAR sequence is similar to the main heparin-binding site (RARKKNKNC, SEQ ID NO: 3) of bone morphogenetic protein 4 (BMP4). The CAR phage homed 100 to 140 fold more efficiently to wounds in the patellar and Achilles tendons and in the skin than non-recombinant. To confirm the specificity of the homing for wound tissue, wounds were induced in the patellar and Achilles tendons of the left hind limb, while subjecting the right hind limb to a sham operation. The sham operation consisted of a skin incision that exposed the tendon but left it otherwise intact. When tested on day 5 after wounding, the CAR phage homed 220 to 370 fold more to the wounded tendons compared to the contra-lateral intact tendons and to wounded skin compared to intact skin distant from the wound sites. In contrast, similar numbers of the CAR phage and control phage accumulated in liver, kidney, heart, lung and spleen.

A CRKDKC(CRK, SEQ ID NO: 2) peptide was identified from skin wounds in two independent screens. The CRK sequence is completely identical to the portion of the thrombospondin type I repeats (TSR I) which are present in a large number of extracellular matrix proteins. The sequence is shorter than the structure of the $CX_7C$-library would predict; a modified peptide structure is a relatively common occurrence in phage screening (Hoffman et al. 2003). The sequence contains a cysteine residue at both ends; these cysteines are likely to form a cyclizing disulfide bond. Intravenously injected CRK phage homed to 5-day tendon and skin wounds approximately 50 times more than non-recombinant control phage. Comparison to the corresponding healthy tissues on the contra-lateral side showed nearly 80-fold preference for tendon and skin wounds. Similar numbers of the CRK phage and control phage were found in the liver, kidney, heart, lung, and spleen. Finally, both the CAR and CRK sequences were re-cloned into the T7 vector and showed that the resulting phage clones homed to wounds as effectively as the original phage.

ii. Sequence Specificity of Wound Homing by CAR and CRK

In the same tendon wound screen that produced the CAR sequence, a peptide was found with a somewhat related sequence, CARSTKATC (CAR2, SEQ ID NO: 4). We also created a CAR mutant phage by changing two basic amino acids to neutral ones (CARSKNKDC mutated to CAQSANKDC, SEQ ID NOS: 5 and 6, respectively). Both CAR2 and the mutant phage showed impaired wound-homing properties: the CAR2 phage had about 20% of the homing activity of CAR and the mutant phage was essentially inactive in homing. A mutant CRK phage was made by changing two amino acids (from CRKDKC to CRASKC, SEQ ID NO: 7 and 8, respectively). The mutant phage had also almost completely lost the homing ability. The loss of activity as a result of the sequence changes emphasizes the role of the basic amino acids in the homing activity and attests to the specificity of the homing.

iii. Synthetic CAR and CRK Peptides Accumulate in Wounds

The CAR and CRK peptides were synthesized as fluorescein (FITC) conjugates and tested their tissue distribution after intravenous injection to mice and rats with tendon and skin wounds. Both peptides produced strong fluorescent signal in the wounds that co-localized with CD31-positive cells at 4 and 8 hours after the injection. CAR2, even though slightly active at the phage-homing level, produced no accumulated fluorescence, and an unrelated 5 amino-acid control peptide (KAREC, SEQ ID NO: 9) also gave no detectable signal in the wounds. Because of an autofluorescent background in wounds, the fluorescein-labeled peptides were also detected with an anti-FITC antibody, and the signal was thus amplified and converted to a non-fluorescent dye. The antibody staining confirmed the localization of the fluorescein label in the granulation tissue, particularly at later time points, when the fluorescent signal was weak. The fluorescent signal produced by CAR and CRK in non-tumor tissues (liver, kidney, lung and spleen) did not differ from that of the fluorescein-labeled CAR2 or KAREC peptides used as controls.

iv. Healing Stage-Dependent Changes in Phage Homing

As a wound matures, much of the initially rich vasculature gradually regresses. To determine to what extent our wound-homing peptides would home to wounds at times other than the 5-day time point, individual phage clones were injected at days 7, 10 and 14 after wounding. The total number of homing phage rescued from the wounds decreased as wound healing progressed, presumably reflecting less dense vascularization of the wound tissue. Surprisingly, the CRK phage, which homed less strongly than CAR at day 5, was generally the more efficient homing peptide at the later stages of wound healing. Phage staining showed that both phage clones co-localized with blood vessels at all stages in wound healing. In agreement with the phage homing data, the CRK phage gave stronger staining of the wound vessels than CAR phage. The phage staining indicates that the molecular change reflected in the relative homing of CAR and CRK resides in the vasculature.

v. Cell Surface Heparan Sulfate as the Target Molecule for CAR

The CAR sequence homology with the heparin-binding site of BMP4 and the presence in CRK of a classical heparin-binding motif (XBBXBX; where X denotes any amino acid and B basic residue, SEQ ID NO: 10), showed that a particular form of a glycosaminoglycan, likely a heparan sulfate, can serve as the binding site for one of both of the peptides. Chinese hamster ovary cells (CHO-K) were used, and the pgsA-745 mutant CHO line that is defective in glycosaminoglycan biosynthesis (Esko et al. 1985)) to test the binding of CAR and CRK to cell surface glycosaminoglycans. CAR phage bound to the CHO-K cells 55-fold more than non-recombinant control phage ($p<0.0001$), but there was no specific binding to the glycosaminoglycan-deficient cells. The CRK phage did not bind significantly to either cell line. Pretreatment of the CHO-K cells with heparinase I and III decreased the binding of the CAR phage by almost 80% ($p<0.0001$). The CAR phage also bound to heparin-coated beads; 70 fold more CAR phage than non-recombinant control phage was recovered from the beads ($p<0.0001$). CRK phage binding was only marginally higher than that of the control phage.

FACS analysis also revealed strong binding of the synthetic CAR peptide to the CHO-K cells, but not to the pgsA-745 cells. An excess of unlabeled CAR peptide inhibited the binding in a dose-dependent manner. The binding could also be inhibited with the CAR phage. The CAR2 peptide bound only weakly to the CHO-K cells, and KAREC showed no binding to either the CHO-K or pgsA-745 cells. These results indicate that CAR, but not CRK, has an active heparin-binding site, and that CAR binds to glycosaminoglycan moiety in cell surface heparan sulfate proteoglycans (HSPGs).

vi. Cell-Penetrating Properties of CAR Peptide

Many of the best-characterized cell penetrating peptides contain basic residues, and HSPGs are thought to be involved in the internalization of these peptides (Joliot 2005; Zorko 2005). This prompted the study of cell-penetrating properties of the wound-homing peptides. Fluorescein-labeled CAR peptide incubated with CHO-K cells accumulated within 30 min inside the cells, overlapping with the nucleus. Confocal microscopy confirmed the nuclear localization. The CRK peptide bound to the cells, but was not detectably internalized. CAR2 showed no binding or internalization. Thus, the CAR peptide appears to be a cell-penetrating peptide. It was demonstrated that internalization of the CAR peptide by CHO-K cells takes place. FITC-conjugated CAR, CAR2, CRK, KAREC, CGKRK, and F3 peptides (10 µM) were incubated with CHO-K for 4 hours, the cells were washed, fixed, stained with the nuclear stain, DAPI, and examined by confocal microscopy. The CAR peptide produces strong green fluorescence that mostly overlaps with nuclear DAPI staining. CAR2, CRK, and KAREC peptides give no detectable fluorescence. CGKRK and F3 overlap with the nuclei and the cytosol. It was demonstrated that internalization of the CAR peptide takes place by human umbilical vein endothelial cells (HUVECs). CAR, CAR2, CRK and KAREC peptides (10 µM) were incubated with HUVECs for 24 h, unbound peptide was removed by washing, and the cells were fixed. The nuclei were visualized by staining with DAPI and the slides were mounted for analysis under an inverted fluorescence microscope. The CAR peptide binds to cells and appears to enter the cells co-localizing with the nuclei. The CRK peptide binds to the cells, but does not internalize. The control peptides show no binding to the cells.

Two cell-penetrating peptides, CGKRK and F3, have been characterized, which specifically recognize angiogenic endothelial cells and tumor cells (Hoffman 2003; Porkka 2002). Each of these peptides contains basic residues, raising the question whether they might bind to the same sites at the cell surface as the CAR peptide. F3 and GCKRK accumulated in the cytosol and nuclei both in the CHO-K and pgsA-745 cells, whereas CAR only binds to and is internalized by the CHO-K cells (and CRK does not bind significantly to either cell line). Moreover, a 10-molar excess of unlabeled F3 or CGKRK peptide did not detectably affect the uptake fluorescein-labeled CAR peptide by the CHO-K cells. Taken together with the demonstration that the receptor for the F3 peptide is cell surface-expressed nucleolin, rather than heparan sulfate, these results show that the specificities of CAR and CRK are new.

vii. Discussion

Two novel peptides are herein reported that specifically home to tendon and skin wounds, targeting both the vasculature and granulation tissue of the wounds. The target molecule of one of the peptides appears to be a cell surface heparan sulfate structure. These peptides are used to provide evidence that the molecular profile of blood vessels in wounds changes as wounds mature.

This approach was based on the notion that in vivo screening of phage libraries using wound-induced angiogenesis as a target can produce a different repertoire of vascular homing peptides than screening on other types of angiogenic lesions, such as tumors, which have been used extensively in similar screening (Ruoslahti 2002). This hypothesis was shown to be correct. The wound-homing peptides contain several basic residues, and highly basic peptides have been previously identified in tumor screens (Hoffman 2003; Joyce 2003). Moreover, the CAR and CKR peptides also recognize tumor vasculature. However, the arrangement of the basic amino acids and other sequence features distinguish these new peptides from the previously described ones. They also differ in heparin binding and cell-type specificity. Among the earlier peptides, F3 and CGKRK bind to heparin, but as shown here, are equally effective in binding to cells that express cell surface heparan sulfate and cells that lack it. In contrast, CAR does not recognize the heparan sulfate-deficient cells, and CRK does not bind to heparin.

The phage screening was performed using wounds made in two tissues, tendon and skin. The CAR peptide came from a tendon screen and the CRK peptide was obtained in a skin screen. Despite their different origin, both peptides homed to wounds in both tissues.

The CAR and CRK peptides displayed an opposite homing preference with regard to the age of the wound; CAR favors early wounds and CRK mature ones. The CAR and CRK phage exclusively accumulate in the blood vessels of the wounds, as shown by nearly complete overlap of phage immunostaining with the blood vessel marker CD31. It is concluded that wound maturation is accompanied by changes in the profile of molecular markers in wound blood vessels. This conclusion parallels what has been observed in studies on tumor vasculature. Vascular markers can distinguish the blood vessels and lymphatics in pre-malignant lesions from those of fully malignant tumors in the same tumor system (Joyce 2003; Zhang 2006). Furthermore, blood vessels in tumors at different stages of tumor development and different stages of vessel maturation differ in their response to anti-angiogenic treatments. The results show that a similar maturation process takes place in wound vasculature.

The CAR peptide binds to heparin and cell surface heparan sulfate, showing that one or more HSPGs at the cell surface are the target molecules for this peptide. HSPGs are ubiquitously expressed, but sequence variability in their heparan sulfate component makes possible tissue and cell type-specific interaction with proteins. The specificity of the CAR peptide for wound vessels and tumor vessels shows that this peptide may recognize a heparan sulfate sequence specific for wound and tumor angiogenesis.

viii. Experimental Procedures a. Materials

Heparinase I (flavobacterium heparinum; heparin lyase, EC 4.2.2.7), heparinase III (F. heparinum; heparin-sulfate lyase, EC 4.2.2.8) and heparin immobilized on acrylic beads were purchased from Sigma (St. Louis, Mo.).

b. Generation of Wounds

Wound experiments were carried out in 6-8-week old male Sprague-Dawley rats and BALB/c mice. Rats were anesthetized with an intraperitoneal injection of 50/50% ketamine-Xylaxine, and intraperitoneal injection of 2.5% avertin was used for mice. Skin was shaved, cleaned and disinfected with betadine and 70% alcohol. All animal experiments were approved by the IACUC of Burnham Institute for Medical Research.

Two types of injuries were used with patellar tendons: For phage screening in rats, patellar tendons were exposed through small skin incisions placed on the lateral side of the joint so that the skin wound and tendon wound were not in direct contact with each other. Six longitudinal, full-length incisions were made into the tendon. Full-thickness incision wounds, 1.5 cm in length, were made in skin on the back of the animal. The skin wounds were left uncovered without a dressing. For quantification of phage homing and peptide injections, two size 11 surgical scalpels were placed side-by-side and the central third of the patellar tendon was removed analogous to the graft used in anterior cruciate ligament reconstruction. Achilles tendons were wounded by making four longitudinal, full-length incisions into the tendon. Skin wounds were 8 mm circular, full-thickness excision wounds, made to the skin with a biopsy punch. None of the procedures prevented the animals from bearing weight and moving immediately after the operation and without a noticeable limb.

c. Phage Libraries and Library Screening

The libraries were prepared by using NNK-oligonucleotides encoding a random library of cyclic peptides of the general structure $CX_7C$, which were cloned into the T7Select 415-1 vector according to the manufacturer's instructions (Novagen, Madison, Wis.). This vector displays peptides in all 415 copies of the phage capsid protein as a C-terminal fusion.

The screening process involved three in vivo-selection rounds. Eight-week-old Sprague-Dawley rats were injected with the library through the tail vein or intracardially and were perfused 10 min later through the heart with 1% BSA in DMEM to remove unbound intravascular phage. The first in vivo round included 19 animals with both patellar tendon and skin wounds, which were separately pooled. The second round used separate sets of 3 animals for tendon and skin wound screening, and the third round was performed with one wound of each kind.

d. Peptides

Peptides were synthesized with an automated peptide synthesizer by using standard solid-phase fluorenylmethoxycarbonyl chemistry. During synthesis, the peptides were labeled with fluorescein with an amino-hexanoic acid spacer. Each individual fluorescein-conjugated peptide was injected intravenously into the tail vein of rats or mice with wounds. The peptides were allowed to circulate for different periods of time, followed by heart perfusion. Tissues were embedded into OCT (Tissue-Tek) and processed for microscopy.

e. Immunohistochemistry

Frozen tissue sections were fixed in acetone for 10 min and incubated with 0.5% blocking reagent for 1 hour (NEN Life Sciences, Boston, Mass.). Tissue sections were incubated with the primary antibody overnight at 4° C. The following monoclonal (mAbs) and polyclonal antibodies (pAbs) were used: rabbit anti-T7-phage affinity-purified pAb (1:100) [33], rat anti-mouse CD31 mAb (1:200; BD Pharmingen) and rabbit anti-FITC pAb (1:200, Invitrogen, Carlsbad, Calif.). The primary antibodies were detected with labeled secondary antibodies, and each staining experiment included sections stained with species-matched immunoglobulins as negative controls. The sections were washed several times with PBS, mounted in Vectashield Mounting Medium with DAPI (Vector Laboratories) and visualized under an inverted fluorescent or light microscope.

f. Cell Culture

Chinese hamster ovary cells (CHO-K) were obtained from the American Type Culture Collection (Rockville, Md.). The pgsA-745 mutant cell line is derived from CHO-K. Cells were maintained in αMEM Earle's salt supplemented with 10% fetal bovine serum, 100 µg/ml streptomycin sulfate, 100 units of penicillin G/ml and 292 µg/ml L-glutamine (Invitrogen, Carlsbad, Calif.). HUVECs were cultured according to the manufacturer's instructions (Cambrex, East Rutherford, N.J.).

g. Cell Binding Assays

Cells were detached with 0.5 mM EDTA solution (Irvine Scientific, Santa Ana, Calif.), washed with PBS and re-suspended in 1% BSA+αMEM. For the phage binding experiments, approximately $1 \times 10^{10}$ phages were added to 15 ml culture media containing approximately $1 \times 10^6$ cells in a test tube. The samples were rotated for 2 hours at +4° C. The cells were then washed six times and transferred to new tube. After a final wash, the cells were counted and cell-bound phage titers were determined. Heparinase treatment of the CHO-K cells was carried out using 1.5 IU/ml heparinase I and 1.25 IU/ml heparinase III in serum-free culture media for 2 hours.

Peptide binding to cells was studied essentially as described above for phage. Peptides were tested at 5 µM concentration, with or without $5 \times 10^9$ phage. After incubation on ice for 30 min, the cells were washed and resuspended with PBS containing 2 µg/ml of propidium iodide (PI, Invitrogen, Carlsbad, Calif.) and analyzed using a FACScan flow cytometer (BD, San Jose, Calif.).

To study peptide internalization, CHO-K cells or HUVEC seeded on plastic coverslips were incubated with 10 µM fluorescein-conjugated peptides for 30 min to 72 hours, washed 3 times with PBS, and fixed with 4% paraformaldehyde for 20 min at room temperature. After several washes with PBS, the nuclei were visualized by staining with DAPI, and the slides were mounted with ProLong Gold antifade reagent (Invitrogen, Carlsbad, Calif.). The images were acquired using Olympus IX81 inverted and Olympus Fluoview FV1000 confocal microscopes. Z-stack images were taken by confocal microscope every 1 µm through the cells.

h. Heparin Binding

To measure phage binding to heparin, heparin-coated acrylic beads 10% (v/v) were suspended in 20 mM $Na_2HPO_4$ buffer, pH 7.2, containing 0.2 M NaCl. Approximately $5.0 \times 10^9$ phage particles were incubated with the beads for 1 hour at room temperature. The beads were washed, transferred to new tube and, bound phage was eluted with 1.2 M NaCl (pH 7.2) and titrated.

i. Statistical Analysis

Differences between the various treatments were statistically tested using the Student's unpaired t-test, while the phage homing to wounds versus sham-operated tissues was analyzed using the Student's paired t-test. For comparisons of multiple groups, statistical analysis was carried out by two-way analysis of variance (ANOVA) complemented by the Bonferroni post hoc test for pair-wise comparisons between the test groups. The possible difference in the homing of the different phage clones to wounds was assessed using the log-transformed variables. P values of less than 0.05 were considered statistically significant for all tests. The significance level shown refers to two-tailed test.

2. Example 2

Target-Seeking Anti-Fibrotic Compound Enhances Wound Healing and Suppresses Scar Formation Tissue injuries caused by trauma, surgery and inflammation are a major medical problem. Options in promoting tissue repair are largely limited to local intervention. We have designed a target-seeking biotherapeutic for systemic wound healing applications. The strategy uses two peptides that specifically recognize blood vessels in wounds and can deliver a payload to wounds with a 50- to 500-fold selectivity. We use these peptides to deliver decorin, into skin wounds. Decorin prevents tissue fibrosis (Border 1992; Fukushima 2001; Weis 2005; Jarvelainen 2006) and promotes tissue regeneration (Davies 2004) by inhibiting TGF-β activity (Yamaguchi 1990; Yamaguchi 1988) and by some other regulatory activities (Reed 2002; Zhang 2006). Proteins in which decorin is fused to a wound-homing peptide were strikingly effective in preventing scar formation where an equivalent dose of decorin was inactive. Thus, selective physical targeting, which is referred to as 'synaphic' (Greek: together; affinity) delivery, yields a wound-healing compound with an enhanced specificity and potency. This approach can make systemic enhancement of tissue repair a feasible option.

It is difficult to maintain bioactivity of locally applied therapeutic agents because of problems with lack of retention of the agent in the wound, poor tissue penetration, and instability of protein therapeutics in the protease rich environment of the wound. Moreover, deep injuries and multiple sites of injury further limit the usefulness of local treatment. Clearly, systemic approaches to tissue repair is valuable. The response to tissue injury in adult mammals seems to be focused on quick sealing of an injury, which results in scar formation. The proliferation of fibroblasts (astrocytes) and smooth muscle cells and enhanced extracellular matrix production by these cells are the main elements of scar formation, which limits regeneration in adult tissues (Singer 1999; Martin 1997). In contrast, fetal tissues heal by a process that restores the original tissue architecture and results in no scarring. Transforming growth factor-β (TGF-β), which is inhibited by decorin, is a major factor responsible for wound repair, but its activity also results in scar formation and fibrosis (Werner 2003; Brunner 2004; Leask 2004).

Figure 4:
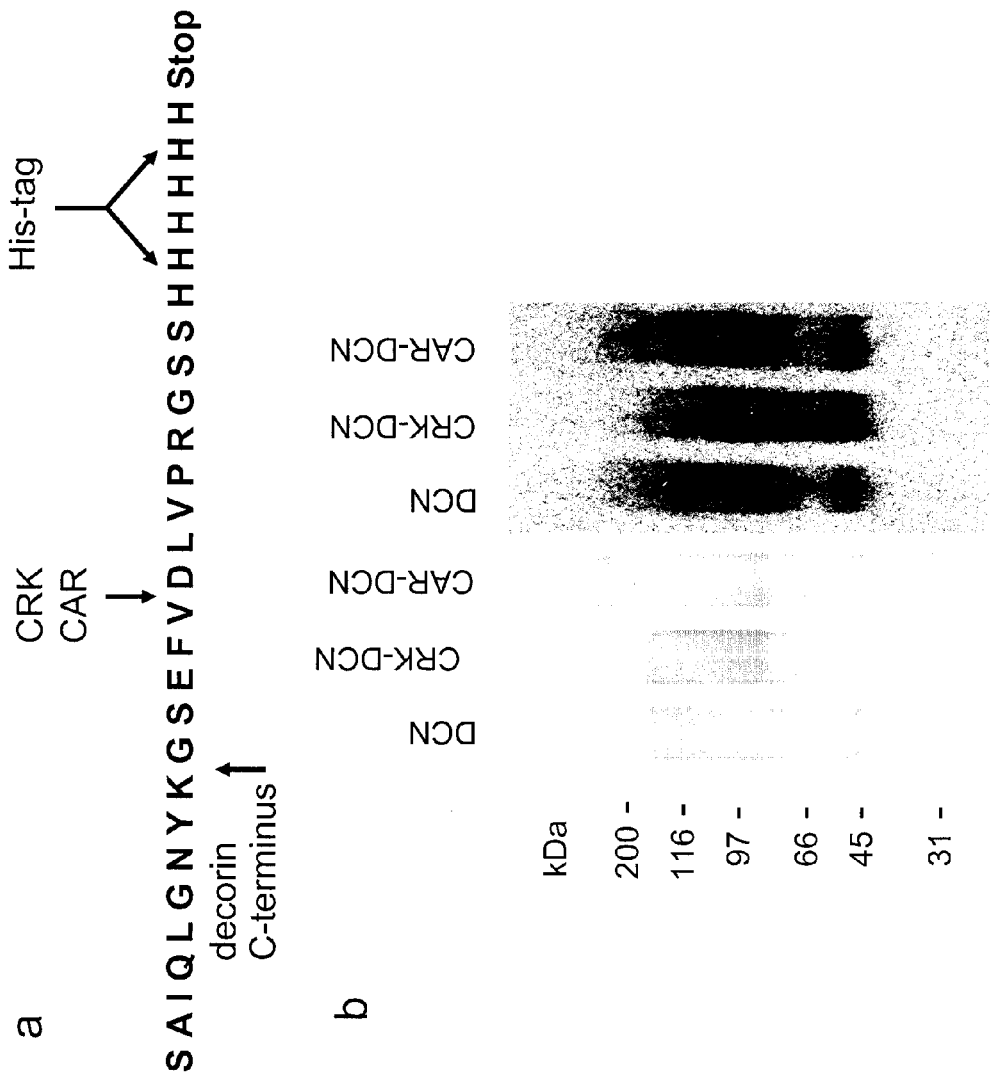
FIG. 4 shows cloning and production of decorin fusion proteins. (a) A schematic showing the fusion (SEQ ID NO:19) of the CAR or CRK peptide sequence and a his-tag to C-terminus of full-length human decorin cDNA. (b) Gel electrophoretic analysis of recombinant decorins. The recombinant proteins were expressed in mammalian cells, purified on a Ni-column, separated on gradient SDS-PAGE gels, and stained with Coomassie Blue (left) or detected with a monoclonal anti-6-histidine tag antibody (right). The decorin-homing peptide fusions migrate as sharp bands at 45 kDa with a smear above it. The sharp bands correspond to the core proteins, and the smear is caused by heterogeneity in the chondroitin sulfate chain attached to most of the molecules. Mass spectrometry confirmed protein identity as decorin, and differential scanning calorimetry produced a sharp peak with a melting temperature of Tm=49.3° C., indicating native protein folding. The yields were 30-55 mg of glycosylated, purified protein per liter of cell culture media.
Figure 5:
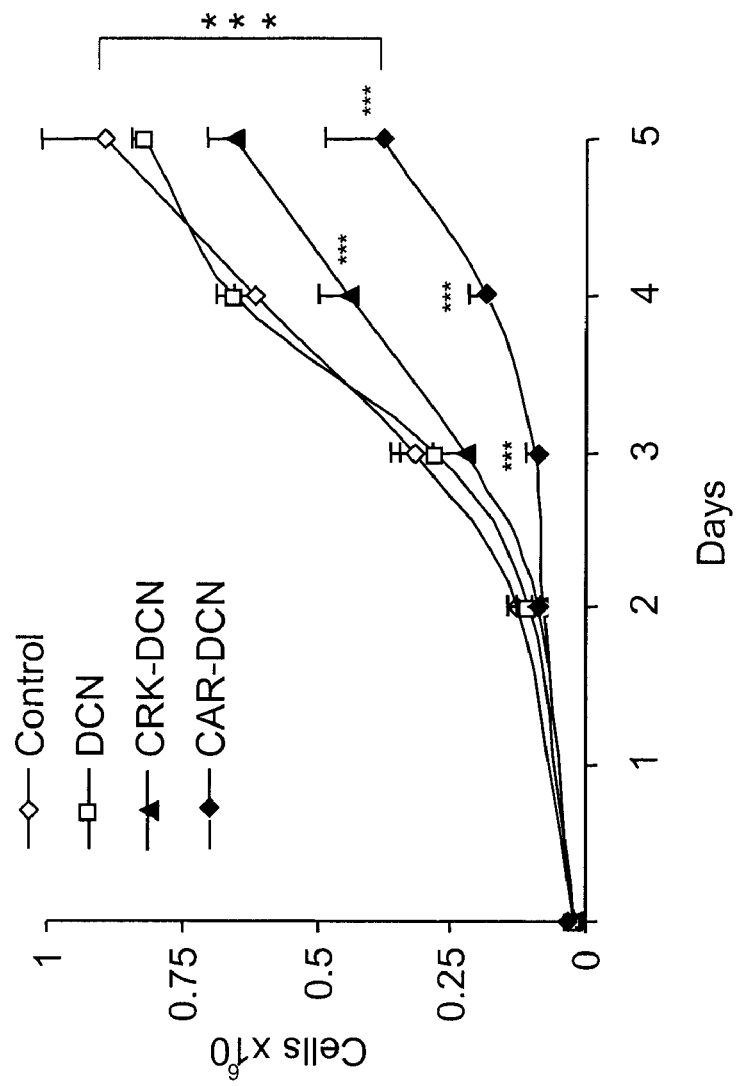
FIG. 5 shows decorin-homing-peptide fusion proteins inhibit CHO-K cell proliferation. Shown are growth curves of CHO-K cells treated with 0.3 μg/ml/day of decorins; Control, no addition; DCN, decorin; CRK-DCN, CRK-decorin; CAR-DCN, CAR-decorin. Error bars represent mean±standard deviation (SD) of 3 separate experiments performed in duplicate at each time point. CAR-decorin was particularly potent in inhibiting cell proliferation ($P<0.001$ compared to decorin for all doses at each time point after day 3; ANOVA). CRK-decorin was also significantly more potent than decorin ($P=0.017$ on day 5).
Figure 6:
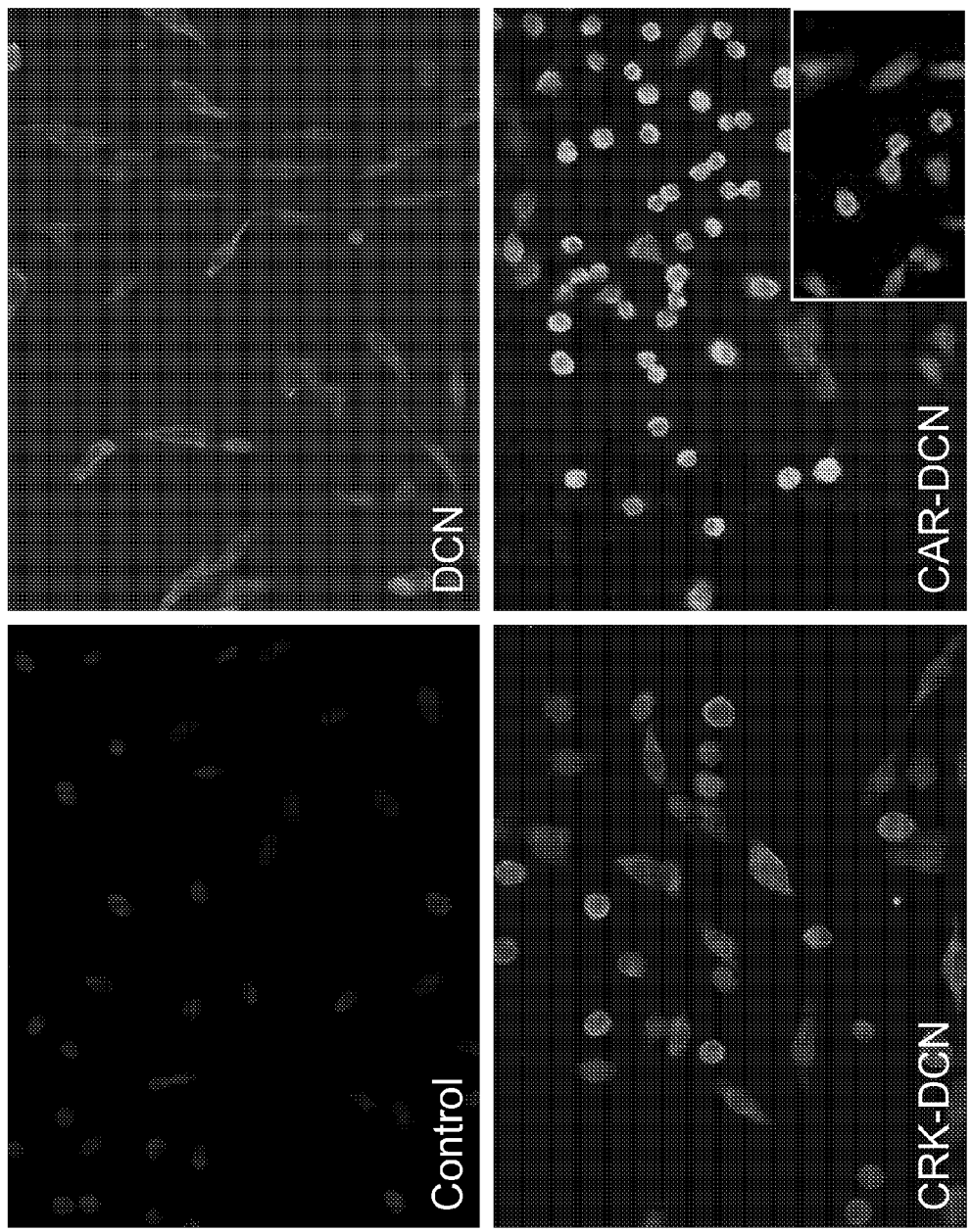
FIG. 6 shows internalization of decorins and inhibition of cell spreading. The culture media of CHO-K cells supplemented with 0.3 μg/ml of the indicated proteins daily for 3 days. The decorins were detected with anti-his-tag antibody and FITC-conjugated secondary antibody. Confocal microscopy confirmed the presence of CAR-decorin fluorescence in the nucleus (inset). Magnification: 400×. The peptide-modified decorins inhibited cell spreading more strongly than unmodified decorin.

Two recombinant wound-targeted decorin fusion proteins were produced by adding one of two wound homing peptides, CRK (CRKDKC, SEQ ID NO: 2) and CAR (CARSKNKDC, SEQ ID NO: 1) to the C-terminus of human decorin (FIG. 4). In accordance with earlier results, decorin inhibited the proliferation of the CHO-K cells at high concentrations, but the homing peptide-modified decorins were highly active at concentrations where decorin was inactive (FIG. 5). They also inhibited cell spreading (Sullivan 2006) more potently than non-modified decorin (FIG. 6). These results show that the peptides impart their binding specificity to the fusion protein decorins, which retain known decorin activities and can be more potent than decorin itself.

When injected intravenously homing peptide decorins consistently produced a 5-fold stronger decorin immunoreactivity in both wound blood vessels and granulation tissue than non-modified decorin (FIG. 1). The underlying normal muscle immediately beneath the skin wound was almost completely negative for immunoreactivity, as was normal dermis and epidermis (shown for CRK-decorin in muscle in FIG. 1). The accumulation of the homing peptide decorins in wound tissue parallels the results obtained in using the same homing peptides to deliver bacteriophage and fluorescein into wounds. The results show that homing peptide-enhanced delivery can markedly increase the concentration of decorin in wounds.

Next, the effect of the homing peptide decorins on wound healing was examined. The daily dose of 40 μg/day was chosen based on previous decorin studies (Seidler 2006; Yang 1999). The dose was doubled on Days 4-6, coincident with the peak in TGF-β expression in wounds (Brunner 2004; Yang 1999). The treatments were started on Day 3 after wounding, when granulation tissue first forms in wounds (Brunner 2004), and continued for 7,9, or 11 days in three independent treatment experiments. Several parameters commonly used to assess wound repair and scarring were measured (Ashcroft 1999; Cheon 2006; Shah 1995).

Figure 2A:
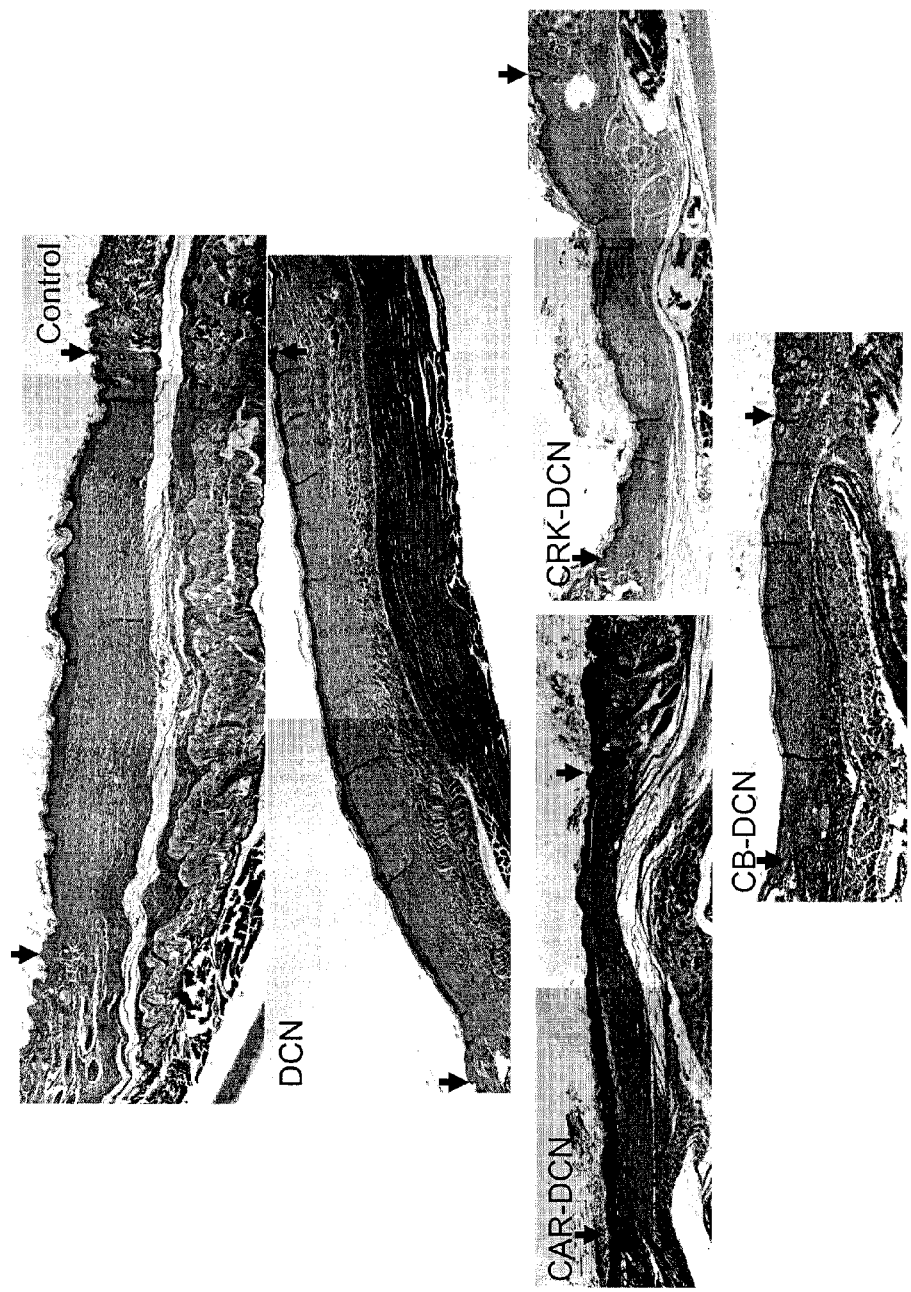
FIG. 2 shows a reduction in granulation tissue, scar formation, and wound width during wound healing in mice treated with homing peptide decorins. (a) Representative microscopic fields from the wounds of animals on Day 14. The area of granulation tissue/scar (b) and hyperproliferative epidermis (c) was quantified by examining two such microscopic sections from each wound and expressed as the average of the two values. There were seven animals, each with three wounds, in every treatment group. (*) $P<0.05$, () $P<0.01$, (*) $P<0.001$, ANOVA. The results are expressed as mean±SEM. CRK and CAR refer to the free peptides. (d) Rate of wound re-epithelialization. The wounds were examined and photographed daily. Re-epithelialization was recorded and expressed as percentage of completely closed wounds. Statistical significance was examined using the $\chi 2$ test, (*) $P<0.05$, () $P<0.01$, (*) $P<0.001$.
Figure 2B:
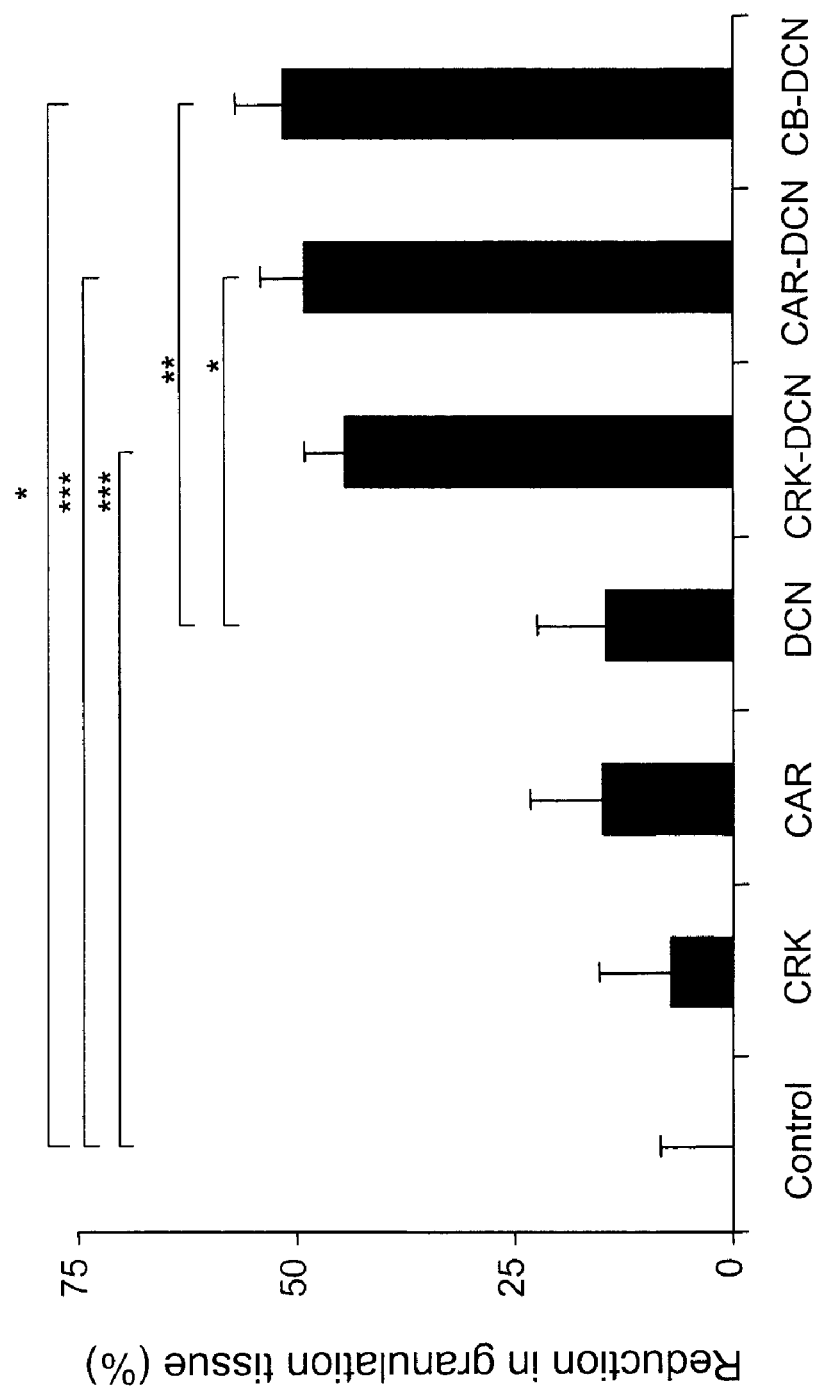
Figure 2C:
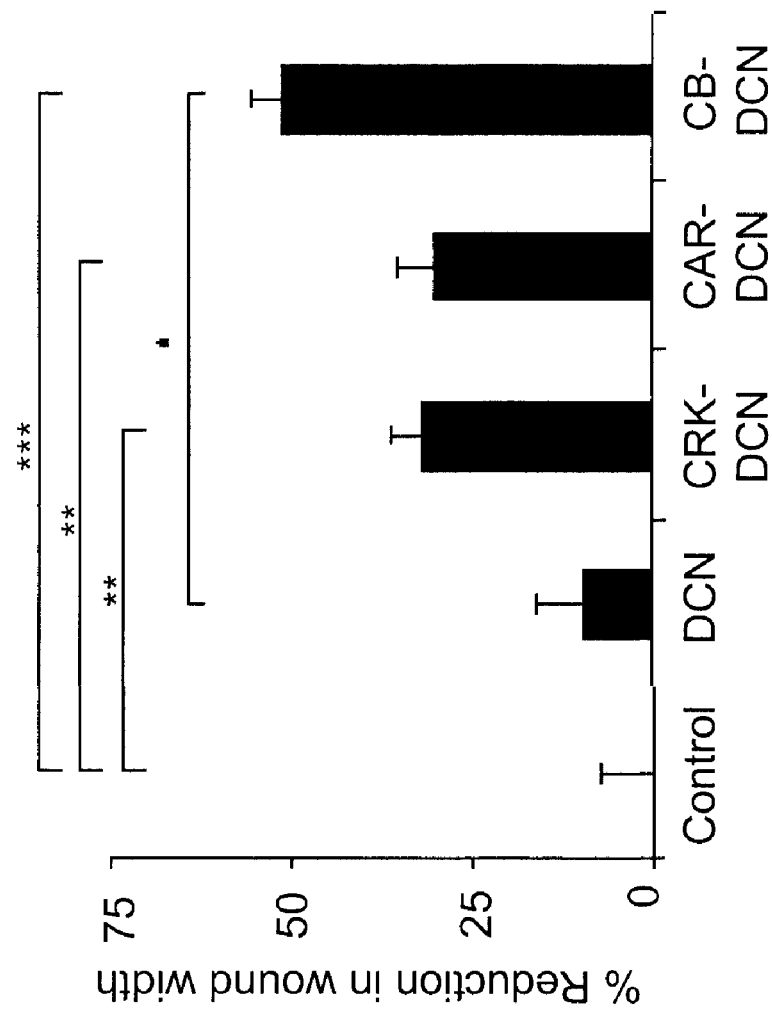
Figure 2D:
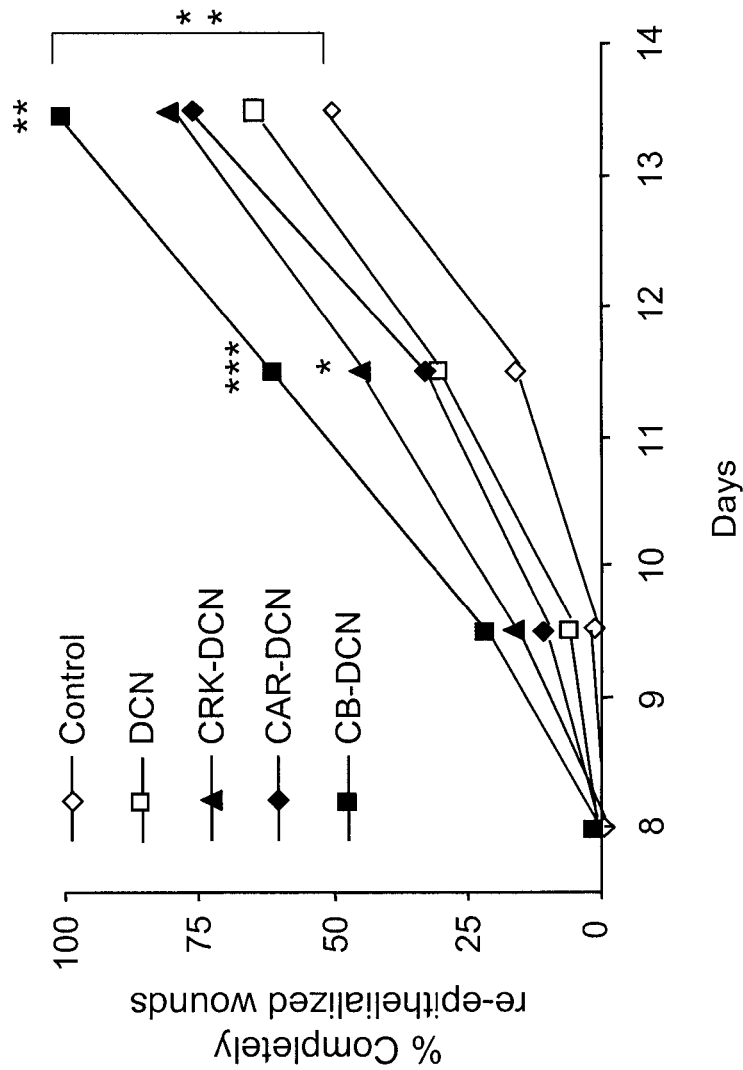

Histological analysis showed that the granulation tissue/scar area in the wounds was strikingly smaller in all groups that received homing peptide decorins. Representative micrographs and quantification of granulation tissue from wounds at Day 14 after the wounding are shown in FIG. 2. The homing peptide decorins reduced the wound area by approximately 50% relative to control groups. Non-modified decorin, or the homing peptides alone, produced no statistically significant changes. Wound width (the width of hyperproliferative epidermis) was also significantly decreased in groups receiving homing peptide decorins (FIG. 2c). Re-epithelialization was accelerated by the homing peptide decorins; the result was highly significant for a CRK-decorin/CAR-decorin combination (FIG. 2d).

Figure 3:
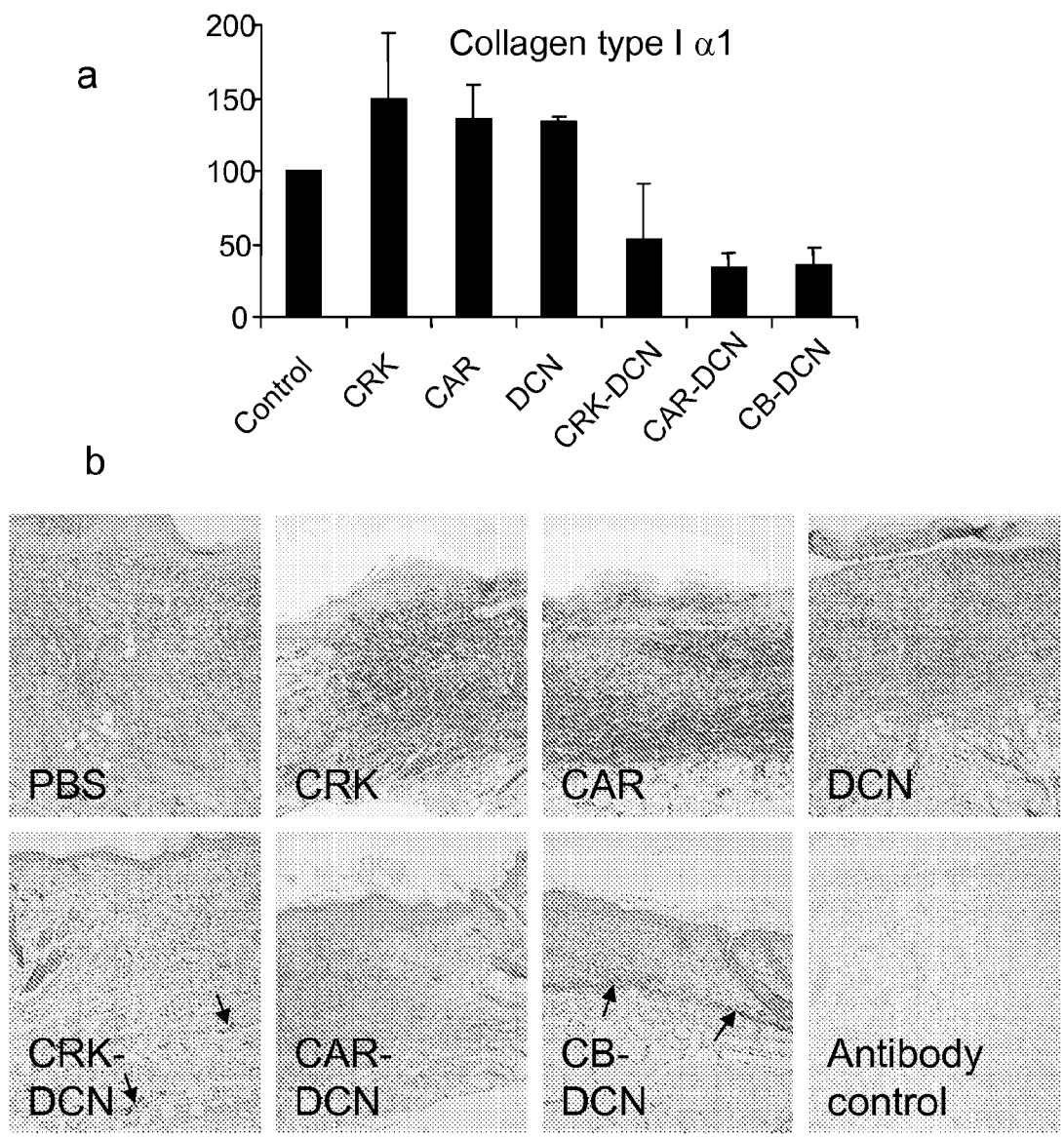
FIG. 3 shows the effect of decorins on TGF-β-induced processes in skin wounds. (a) Gene expression. Wounds produced and treated as in FIG. 2 were harvested on Day 5 and mRNA expression for collagen type I α1 gene was determined. The PBS treatment control was assigned the value 100%. Error bars represent mean±SD for two pools of RNA isolated from two wounds in each of four different animals. (b) Accumulation of α-SMA-positive (myofibroblasts). Representative sections from wounds collected on Day 10 after wounding are shown. A wound from a decorin-treated mouse was stained with class-matched mouse IgG as a specificity control (Antibody control). The wounds of mice treated with CAR-decorin showed diminished myofibroblast reaction and there were almost no myofibroblasts in the wound stroma of mice treated with CRK-decorin and CB-decorin; the arrows indicate α-SMA-positive smooth muscle cells in the walls of blood vessels. Magnification: ×150.
Figure 7:
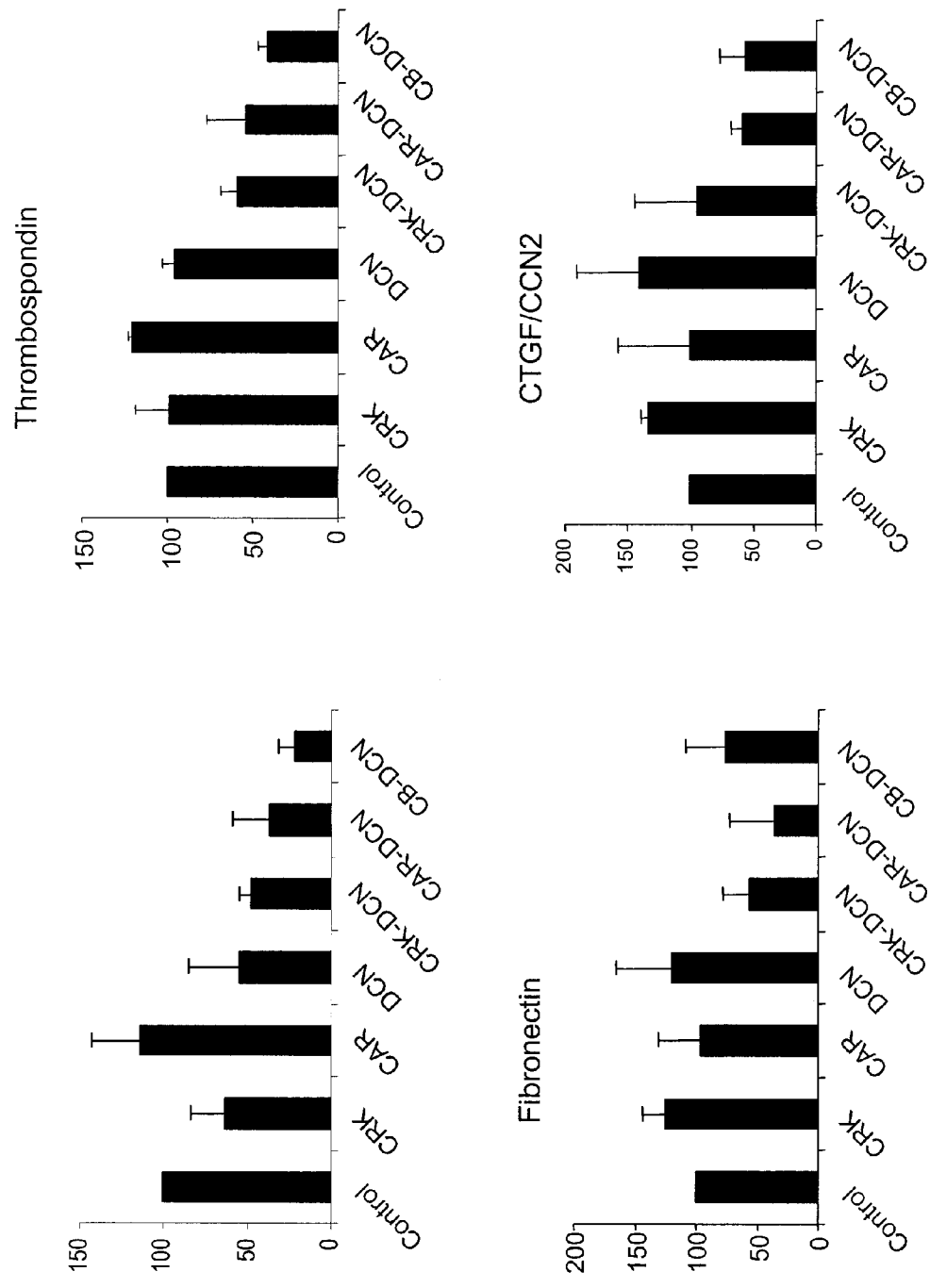
FIG. 7 shows the effect of decorins on the expression of TGF-β-induced genes in skin wounds. Wounds produced and treated as in FIG. 2 were harvested on Day 5 and mRNA expression for the indicated genes was determined. The PBS treatment control was assigned the value 100%. Error bars represent mean±SD for two pools of RNA isolated from two wounds in each of four different animals.

TGF-β is likely to be an important target of decorin because it plays a key role in scar formation (Werner 2003; Brunner 2004; Leask 2004; Ashcroft 1999), and decorin inhibits TGF-β-dependent responses (Border 1992; Yamaguchi 1990; Yamaguchi 1988; Hildebrand 1994). The homing peptide decorins inhibited gene expression of several TGF-β-induced genes that play are associated with scar formation (Leask 2006; Grotendorst 2005; Border 1990). The inhibition was about 50% at day 5 of healing, when TGF activity peaks in wounds (FIGS. 3a and 7). The transformation of fibroblasts to α-SMA-positive myofibroblasts, which is TGF-β-dependent and responsible for converting granulation tissue to permanent scar tissue (Desmouliere 2005) was greatly reduced at later time-points (FIG. 3b).

TGF-β stimulation of fibroblast growth and extracellular matrix production is primarily mediated by CTGF/CCN2, which is one of the genes found to be down-regulated by the homing peptide decorins. However, to enhance the proliferation of wound fibroblasts, CCN2 requires the presence of epidermal growth factor (EGF). Interestingly, decorin also antagonizes EGF by binding to EGF receptors (Iozzo 1999; Santra 2000). Thus, wound-targeted decorin, by virtue of being able to block both TGF-β and EGF signaling, may be superior to therapeutic approaches that only inhibit TGF-β. Moreover, decorin can to be a physiological regulator of scar formation, as decorin expression is induced in inflamed tissues, and decorin null mice exhibit accentuated scarring.

The CRK and CAR peptides can deliver other payloads to wounds with 40- to 150-fold efficiency relative to the same payload without homing peptide modification. As decorin seems to have an inherent ability to accumulate in wounds (FIG. 5) and tumors, the homing increment provided by the peptides may not be as high as with a neutral payload; tissue staining suggested a 5-fold enhancement of decorin homing.

In general terms, these results show that targeted delivery can extend the use of therapeutic molecules to wounds and traumas inaccessible by topical delivery. This opens Lip new possibilities in traumatology and general surgery.

Mutated TGF-β and EGF-related growth pathways are an important driver of tumor growth in a number of cancers, and TGF-β may play a particular role in progenitor-like cells of breast cancers (Shipitsin 2007). Decorin can inhibit the growth of tumor cells in vitro and suppress tumor growth and metastasis in vivo. The wound-homing peptides also recognize tumor blood vessels and bind to tumor cells. Thus, targeted decorins can also find application in tumor therapy.

i. Methods a. Peptides and Fusion Proteins

Peptides were synthesized with an automated peptide synthesizer by using standard solid-phase fluorenylmethoxycarbonyl chemistry. During synthesis, the peptides were labeled with fluorescein with an amino-hexanoic acid spacer as described (Laakkonen 2002).

The decorin (Krusius 1986) constructs were expressed in 293-F cells using the FreeStyle 293 expression system from Invitrogen (Invitrogen, Carlsbad, Calif.) according to the manufacturer's instructions. The cells were cultured for 48 hrs and the decorins were isolated from the media on Ni-NTA agarose beads (Qiagen, GmbH, Germany) using 5 ml of beads per 500 ml of media. After an overnight incubation at +4° C., the beads were washed with PBS, and decorin was eluted with PBS containing 300 mM imidazole, dialyzed against PBS, and stored at −80° C.

b. Wound Healing Model and Treatment Schedule

Six 8-week-old male BALB/c mice were anesthetized with intraperitoneally-injected 2.5% avertin. Skin was shaved, cleaned, and disinfected with betadine and 70% alcohol. All animal experiments received approval from the IACUC of Burnham Institute for Medical Research. Treatment trials were conducted on mice that had circular, 8 mm-diameter, full thickness (including panniculus carnosus muscle) excision wounds in the dorsal skin. The wounds were first marked by a biopsy bunch and then cut with scissors. All skin wounds were left uncovered without a dressing.

The treatments were started three days after wounding and consisted of daily tail vein injections. The dose for decorins was 40 µg per injection, selected based on previous treatment studies (Border 1992), except that the dose was doubled on Days 4-6 to coincide with the expected peak of TGF-β expression in the wounds. Bovine Serum Albumin (BSA) was used as a control protein. Peptides were administered at 1 µg (2 µg on days 4-6) per injection. For the CRK-decorin-CAR-decorin mixture, the daily dose consisted of 30% CRK-decorin and 70% CAR-decorin between Days 3 and 6. The ratio was reversed from Day 7 based on previously determined homing profiles of CRK and CAR phage to wounds at different timepoints. The wounds were inspected and photographed daily, and scored for complete re-epithelialization. At the end of the treatment period, the animals were sacrificed and the wounds collected and processed for analyses.

Image analysis and quantification of granulation tissue/wound area, and hyperproliferative epidermis were done using ImageJ program (NIH, Bethesda, Mass.). The wounds were cut in the middle, one section from each side of the wound was evaluated, and the average of these two values was used in the analysis. The length of hyperproliferative epidermis and size of the wound tissue were determined from the Masson trichrome stained tissue sections.

Cell culture, binding assays, processing of tissue samples, immunohistochemistry, and real time PCR were performed using standard methods (Supplementary Material).

ii. Statistical Analysis

For comparisons of multiple groups, statistical analysis was carried out by two-way analysis of variance (ANOVA) complemented by the Bonferroni post hoc test for pair wise comparisons between the test groups. In the frequency outcome variable (percentage of complete re-epithelialization), the groups were compared with the $\chi2$ test. P values of less than 0.05 were considered statistically significant. The significance level shown refers to two-tailed test.

iii. Primers for Decorin Cloning

The following primers were synthesized to amplify full-length human decorin cDNA from pGEM1-PG40 cloning vector[1] and to clone EcoR I and Sal I restriction-sites and his-tag into the C-terminus of the decorin: 5'-ACGTGGATC-CATGAAGGCCACTATCATCCTCCTTC-3' (SEQ ID NO: 11) and 5'-ATCCGCTCGAGTTAGTGATGGTGATGGT-GATGCGAGCTGCCGCGCGGCACCAG GTCGAC-GAATTCCGAGCCCTTATAGTTTCCGAGT-TGAATGGCAGA (SEQ ID NO: 12). The resulting PCR-product was then subcloned into baculovirus-expression vector pFastBac1 (Invitrogen, Carlsbad, Calif.). The wound homing peptides were cloned between the C-terminus of the decorin and the his-tag by allowing the following primers to anneal together: CAR; 5'-AATTTTGTGCACGTTCGAA-GAACAAAGATTGCG-3' (SEQ ID NO: 13) and 5'-TC-GACGCAATCTTTGTTCTTCGAACGTGCACAA-3' (SEQ ID NO: 14) and CRK; 5'-AATTTTGCCGGAAG-GATAAGTGCG-3'(SEQ ID NO: 15) and 5'-TCGACG-CACTTATCCTTCCGGCAA-3' (SEQ ID NO: 16). The homing peptide coding sequences were ligated to the EcoR I and Sal I restriction sites. The following primers were synthesized to amplify the resulting construct flanked with a Kozak sequence from the pFastBac1-vector to mammalian expression vector pcDNA3.1/myc-his-C (Invitrogen, Carlsbad, Calif.): 5'-ACGTGGATCCGGACCGTTTCAACA-GAGAGGCTTATTTGACTTTATGCTAGA-3' (SEQ ID NO: 17) and 5'-ATCCGCTCGAGTTAGTGATGGTGATG-GTGATGCGAGCT-3' (SEQ ID NO: 18). A map of the C-terminus of the decorin fusion proteins is shown in FIG. 4.

iv. Characterization of Recombinant Decorins

Decorins were analyzed on SDS-PAGE on 4%-20% acrylamide gradient gels. Some of the gels were stained with Coomassie Blue, while others were used to transfer the proteins to PVDF membrane and immunoblots were performed with monoclonal anti-6-histidine tag antibody (1:1 000, clone 18184, Novus Biologicals, Littleton, Colo.) and goat anti-mouse IgG-HRP (diluted 1:25,000; Bio-Rad, Hercules, Calif.) and then developed using ECL+plus chemiluminescence reagent (Amersham Biosciences, Piscataway, N.J.), according to the manufacturer's instructions.

For mass spectrometry analysis, proteins were separated on 10% SDS-PAGE. Protein bands were detected by silver staining, extracted, and subjected to in-gel trypsin digestion and peptide mass fingerprinting in MALDI-TOF.

Protein folding was examined by differential scanning calorimetry using N-DSC II differential calorimeter (Calorimetry Sciences Corp., Provo, Utah) at a scanning rate of I oK/min under 3.0 atm of pressure. Protein samples were dialyzed against PBS and the analyses were carried out at 1.0 mg/ml of protein with PBS as reference.

Cell Proliferation And Cell Binding Assays

The effect of decorin preparations on CHO-K cell proliferation was determined as described previously (Yamaguchi 1990; Yamaguchi 1988). The cells were grown in media containing fetal bovine serum that had been dialyzed in a dialysis cassette (Pierce, Rockford, Ill.). The cells were plated in duplicate at a density of $2 \times 10^4$ cells per well in 24-well plates and cultured in 600 µl of culture media. Half of the medium was replaced daily with fresh medium containing decorin. Cells were collected by trypsinization, washed and resuspended in 1 ml of PBS containing 2 µg/ml of propidium iodide (PI) and 20,000 CountBright counting beads (Invitrogen, Carlsbad, Calif.), and analyzed by counting 1,000 beads in FACS. Cell number was also determined by hemocytometer.

To study decorin binding and internalization, CHO-K and glycosaminoglycan-deficient pgsA-745 cells seeded on plastic coverslips were incubated with different decorins for 4 to 72 hrs, washed 3 times with PBS, and fixed with 4% paraformaldehyde for 20 min at room temperature. After several washes with PBS, the primary antibodies against human decorin and 6-histidine were applied on slides for one hour at room temperature, and the primary antibodies were detected with AlexaFluor 488 anti-mouse and anti-rabbit IgGs (1:1,000 and 1:3,000, Invitrogen, Carlsbad, Calif.). After several washes with PBS, the nuclei were visualized by staining with DAPI, and the slides were mounted with Pro-Long Gold antifade reagent (Invitrogen, Carlsbad, Calif.). The images were acquired using Olympus IX81 inverted and Olympus Fluoview FV1000 confocal microscopes. Z-stack images were taken by confocal microscope every 1 µm through the cells.

v. Histology

Wound tissues were isolated, bisected, fixed overnight in 10% buffered zinc formalin (Statlab Medical Products, Lewisville, Tex.), dehydrated, and embedded in paraffin. Sections (6 µm) from the middle of the wound were stained with hematoxylin/eosin or using the Masson trichrome procedure, or processed for immunohistochemistry.

vi. Immunohistochemistry

Frozen sections were fixed in acetone for 10 min and pre-incubated with 0.5% blocking reagent for 1 hr (NEN Life Sciences, Boston, Mass.). Formalin fixed, paraffin embedded tissue sections were deparaffinized, incubated with the blocking reagent, and endogenous peroxidase activity was suppressed with hydrogen peroxide. Tissue sections were incubated with the primary antibody overnight at 4° C. The primary antibodies were detected with corresponding secondary antibodies, and each staining experiment included slides stained with species-matched immunoglobulins as negative controls. The slides were washed several times in PBS, mounted in Vectashield Mounting Medium with DAPI (Vector Laboratories) and visualized under an inverted fluorescent or light microscope.

The following monoclonal (mAbs) and polyclonal antibodies (pAbs) were used: mouse anti-human HRP-conjugated α-SMA mAb (clone 1A4, DAKO, Glostrup, Denmark), rabbit anti-6-histidine tag pAb (1:400, clone NB600-318, Novus Biologicals, Littleton, Colo.), and mouse anti-human decorin mAb (30 µg/ml, clone MAB143, R&D Systems, Minneapolis, Minn.).

vii. Real Time PCR

Mice with five-day-old skin wounds were anesthetized and perfused through the heart with 25 ml of ice-cold PBS, after which the granulation/wound tissue was excised under an operating microscope. Approximately 20-30 mg of tissue was treated with RNAlater (Ambion, Inc., Austin, Tex.) to preserve RNA. The tissue samples were immersed in the Trizol reagent (Invitrogen, Carlsbad, Calif.), homogenized using MagNA Lyser (Roche Diagnostics, Indianapolis, Ind.), and prepared for RT-PCR as described (Galang 2004). RT-PCR was performed using an Mx3000p instrument (Stratagene Inc, La Jolla, Calif.) by following the procedures as described in RT Profiler PCR Array user manual (SuperArray Bioscience Corp. Frederick, Md.). Replicate analysis consisted of two pools of RNA isolated from two wounds in each of four different animals.

a. Other Results

The effect of targeted decorins on myofibroblast differentiation was shown during skin wound healing. Differentiated myofibroblasts were visualized with antibody against α-smooth muscle actin (α-SMA) in wounds of mice receiving various treatments. Representative sections from wounds collected at day 10 after the wounding from mice treated with: BSA control; CAR peptide; CRK peptide; decorin, CRK-decorin; CAR-decorin; CB-decorin (a mixture of CAR-decorin and CRK-decorin); and decorin treated wound stained with class-matched mouse IgG. Those animals treated with decorin coupled to the CAR and CRK peptides showed the highest levels of myofibroblast differentiation.

Cloning and expression of decorin-homing peptide fusions were carried out. The CAR or CRK peptide sequence and a his-tag were cloned into C-terminus of full-length human decorin cDNA. Decorin and the homing peptide fusions were expressed in mammalian cells, purified on a Ni-column and analyzed on SDS-PAGE using 10% gels. The proteins were detected with a monoclonal anti-human decorin antibody.

CAR-targeted decorin internalization was confirmed by confocal microscope. CHO-K were first incubated for 72 h, after which BSA, decorin, CRK-targeted decorin and CAR-targeted decorin (0.3 µg) were added for four hours. Decorin molecules were detected with anti-his antibody, which was detected with FITC-conjugated secondary antibody. CAR-targeted decorin internalizes and reverses the spreading out of the tumor cells already within four hours.

CAR-targeted decorin does not internalize to the nucleus when the cells lack heparan sulphate proteoglycans. pgsA-745 mutant CHO line that is defective in glycosaminoglycan biosynthesis were first incubated for 72 h, after which BSA, decorin, CRK-targeted decorin and CAR-targeted decorin (0.3 µg) were added for four hours. Decorin molecules were detected with anti-his antibody, which was detected with FITC-conjugated secondary antibody. CAR-targeted decorin has similar binding pattern to cells as normal decorin and does not internalizes when the cells are devoid of heparan sulphate proteoglycans.

CAR and CRK peptides home to tumors and extravasate to tumor tissue. Fluorescein-conjugated peptides CAR, control peptide CAR2, CRK and control peptide KAREC were intravenously injected into mice with MDA-MB-235 tumor xenografts. Tumor tissue was collected 4 hours later and examined for the presence of the peptides. Blood vessels were stained with CD-31 antibody and the nuclei were stained with DAPI.

CAR and CRK peptides home to hypervascular regions surrounding the tumors and to tumor tissue. Fluorescein-conjugated peptides CAR, control peptide CAR2, CRK and control peptide KAREC were intravenously injected into mice with MDA-MB-235 tumor xenografts. Tumor tissue was collected 4 hours later and examined for the presence of the peptides. Adjacent tissue section were stained for blood vessels (CD-31), while the FITC-labeled peptide was first detected with rabbit anti-FITC followed by biotin-conjugated anti-rabbit IgG to confirm the source of fluorescent signal to be from the FITC-labeled peptide. The sections were then stained with hematoxylin-eosin.

Wound width in mice treated with targeted decorins was shown. The length of the hyperproliferative epidermis was determined from both halves of the wound and expressed as the average of the two values. There were six animals (each with three wounds) in each time point in each treatment group at Day 10 and 12, respectively. Those animals treated with decorin has the narrowest wounds, showing that healing had taken place.

Granulation tissue and scar formation during wound healing in mice treated with targeted decorins was measured. The area of granulation tissue/scar area was determined from both halves of the wound and expressed as the average of the two values. There were five animals (each with three wounds) in each time-point in each treatment group at day 10, 12, respectively. Those animals treated with decorin showed that the most healing had taken place.

Throughout this application, various publications are referenced. The disclosures of these publications in their entireties are hereby incorporated by reference into this application in order to more fully describe the state of the art to which this invention pertains.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

REFERENCES

Altschul, S. F., Madden, T. L., Schaffer, A. A., Zhang, J., Zhang, Z., Miller, W., and Lipman, D. J. "Gapped BLAST and PSI-BLAST: a new generation of protein database search programs." *Nucleic Acids Res* 25:3389-3402 (1997).

Arap, W., Haedicke, W., Bernasconi, M., Kain, R., Rajotte, D., Krajewski, S., Ellerby, H. M., Bredesen, D. E., Pasqualini, R., and Ruoslahti, E. "Targeting the prostate for destruction through a vascular address." *Proc Natl Acad Sci USA* 99:1527-1531 (2002).

Arap, W., Pasqualini, R., and Ruoslahti, E. "Cancer treatment by targeted drug delivery to tumor vasculature in a mouse model." *Science* 279:377-380 (1998).

Ashcroft G S, et al. "Mice lacking Smad3 show accelerated wound healing and an impaired local inflammatory response." *Nat. Cell Biol.* 1:260-266 (1999).

Border W A, et al. "Natural inhibitor of transforming growth factor-beta protects against scarring in experimental kidney disease." *Nature* 360:361-364 (1992).

Border W A, Okuda S, Languino L R, Sporn M B, Ruoslahti E: "Suppression of experimental glomerulonephritis by antiserum against transforming growth factor beta 1." *Nature* 346: 371-374 (1990).

Brunner G, Blakytny R: "Extracellular regulation of TGF-beta activity in wound repair: growth factor latency as a sensor mechanism for injury." *Thromb. Haemost.* 92:253-261 (2004).

Chargé S B P, Rudnicki M A. "Cellular and molecular regulation of muscle regeneration." *Physiol Rev.* 84:209-238 (2004).

Chen Y, Shi-Wen X, van Beek J, Kennedy L, McLeod M, Renzoni EA, Bou-Gharios G, Wilcox-Adelman S, Goetinck P F, Eastwood M, Black C M, Abraham D J, Leask A. "Matrix contraction by dermal fibroblasts requires transforming growth factor-β/activin-linked kinase 5, heparan sulfate-containing proteoglycans, and MEK/ERK: insights into pathological scarring in chronic fibrotic disease." *Am J Pathol*, 167:1699-1711 (2005).

Cheon S S, et al. "Beta-catenin regulates wound size and mediates the effect of TGF-beta in cutaneous healing." *Faseb J.* 20: 692-701 (2006).

Davies J E, Tang X, Denning J W, Archibald S J, Davies S J. "Decorin suppresses neurocan, brevican, phosphacan and NG2 expression and promotes axon growth across adult rat spinal cord injuries." *Eur. J. Neurosci.* 19:1226-1242 (2004).

Desmouliere A, Chaponnier C, Gabbiani G: "Tissue repair, contraction, and the myofibroblast." *Wound Repair Regen.* 13:7-12 (2005).

Esko J D, Stewart T E, Taylor W H. "Animal cell mutants defective in glycosaminoglycan biosynthesis." *Proc Natl Acad Sci USA.* 82(10):3197-201 (1985 May).

Falanga V. "Wound healing and its impairment in the diapetic foot." *Lancet* 366:1736-1743 (2006).

Folkman J. "angiogenesis." *Annu Rev Med* 57:1-18 (2006).

Fukushima K, et al. "The use of an antifibrosis agent to improve muscle recovery after laceration." *Am. J. Sports Med.* 29:394-402 (2001).

Gabbiani G. "The myofibroblast in wound healing and fibrocontractive diseases." *J Pathol* 200:500-503 (2003).

Galang, C. K., Muller, W. J., Foos, G., Oshima, R. G. & Hauser, C. A. "Changes in the expression of many Ets family transcription factors and of potential target genes in normal mammary tissue and tumors." *J. Biol. Chem.* 279: 11281-11292 (2004).

Gerlag, D. M., Borges, E., Tak, P. P., Ellerby, H. M., Bredesen, D. E., Pasqualini, R., Ruoslahti, E., Firestein, G. S. "Suppression of murine collagen-induced arthritis by targeted apoptosis of synovial neovasculature." *Arthritis Research* 3:357-361 (2001).

Gorvy D A, Herrick S E, Shah M, Ferguson M W J. "Experimental manipulation of transforming growth factor-β isoforms significantly affects adhesion formation in a murine surgical model." *Am J Pathol* 167:1005-1019 (2005).

Grotendorst G R, Duncan M R. "Individual domains of connective tissue growth factor regulate fibroblast proliferation and myofibroblast differentiation." *FASEB J.* 19:729-38 (2005).

Grotendorst G R, Rahmanie H, Duncan M R. "Combinatorial signaling pathways determine fibroblast proliferation and myofibroblast differentiation." *FASEB J.* 18:469-79 (2004).

Hoffman J A, Giraudo E, Singh M, Zhang L, Inoue M, Porkka K, Hanahan D, Ruoslahti E. "Progressive vascular changes in a transgenic mouse model of squamous cell carcinoma." *Cancer Cell* 4:383-91 (2003).

Hildebrand A, Romaris M, Rasmussen L M, Heinegard D, Twardzik D R, Border W A, Ruoslahti E. "Interaction of the small interstitial proteoglycans biglycan, decorin and fibromodulin with transforming growth factor β." *Biochem J* 302 (Pt 2):527-534 (1994).

Hu Q, Ueno N, Behringer R R. "Restriction of BMP4 activity domains in the developing neural tube of the mouse embryo." *EMBO Rep* 5:734-739 (2004).

Iozzo R V, Moscatello D K, McQuillan D J, Eichstetter I. "Decorin is a biological ligand for the epidermal growth factor receptor." *J Biol Chem* 274(8):4489-4492 (1999).

Jarvelainen H, et al. "A role for decorin in cutaneous wound healing and angiogenesis." *Wound Repair Regen.* 14:443-452 (2006).

Joliot A. "Transduction peptides within naturally occurring proteins." *Sci STRE* 313:pe54 (2005).

Joyce, J. A., Laakkonen P., Bernasconi, M., Bergers, G., Ruoslahti, E., and Hanahan, D. "Stage-specific vascular markers revealed by phage display in a mouse model of pancreatic islet tumorigenesis." *Cancer Cell* 4:393-403 (2003).

Kolonin M G. Sun J. Do K A. Vidal C I. Ji Y. Baggerly K A. Pasqualini R. Arap W. "Synchronous selection of homing peptides for multiple tissues by in vivo phage display." *FASEB J.* 20:979-81 (2006).

Kreuger, J., Spillman, D. and Lindahl, Ulf. "Interactions between heparan sulfate and proteins: the concept of specificity." *J. Cell Biol.* 174: 323-327 (2006).

Krusius T, Ruoslahti E. "Primary structure of an extracellular matrix proteoglycan core protein deduced from cloned cDNA." *Proc Natl Acad Sci USA* 83(20):7683-7 (1996).

Krusius, T. & Ruoslahti, E. "Primary structure of an extracellular matrix proteoglycan core protein deduced from cloned cDNA." *Proc. Natl. Acad. Sci. USA* 83:7683-7687 (1986).

Laakkonen, P., Porkka, K., Hoffman, J. A., and Ruoslahti, E. "A tumor-homing peptide with a targeting specificity related to lymphatic vessels." *Nat Med* 8:751-755 (2002).

Laakkonen, P., Akerman, M. E., Biliran, H., Yang, M., Ferrer, F., Karpanen, T., Hoffman, R. M., and Ruoslahti, E. "Antitumor activity of a homing peptide that targets tumor lymphatics and tumor cells." *Proc. Natl. Acad. Sci. USA.* 101: 9381-9386 (2004).

Laemmli, U. K. "Cleavage of structural proteins during the assembly of the head of bacteriophage T4." *Nature* 227: 680-685 (1970).

Leask A, Abraham D J: "All in the CCN family: essential matricellular signaling modulators emerge from the bunker." *J. Cell Sci.* 119:4803-4810 (2006).

Leask A, Abraham D J: "TGF-beta signaling and the fibrotic response." *Faseb J* 18:816-827 (2004).

Liu C. Bhattacharjee G. Boisvert W. Dilley R. Edgington T. "In vivo interrogation of the molecular display of atherosclerotic lesion surfaces." *Am. J. Path.* 163:1859-71 (2003).

Lyon M, Rushton G, Gallagher J T. "The interaction of the transforming growth factor-βs with heparin/heparan sulfate is isoform-specific." *J Biol Chem* 272(29):18000-6 (1997).

Martin, P. "Wound healing-aiming for perfect skin regeneration." *Science* 276:75-81 (1997).

Ohkawara B, Iemura S, ten Dijke P, Ueno N "Action range of BMP is defined by its N-terminal basic amino acid core." *Curr Biol* 12: 205-209 (2002).

Pasqualini, R., and Ruoslahti, E. "Organ targeting in vivo using phage display peptide libraries." *Nature* 380:364-366 (1996).

Pilch J, Brown D M, Komatsu M, Järvinen T A H, Yang M, Peters D, Hoffman R M, Ruoslahti E: "Peptides selected for clotted plasma accumulate in tumor stroma and wounds." *Proc. Natl. Acad. Sci. USA* 103:2800-2803 (2006).

Porkka, K., Laakkonen, P., Hoffman, J. A., Bernasconi, M., and Ruoslahti, E. "A fragment of the HMGN2 protein homes to the nuclei of tumor cells and tumor endothelial cells in vivo." *Proc Natl Acad Sci USA* 99:7444-7449 (2002).

Rajotte, D., Arap, W., Hagedorn, M., Koivunen, E., Pasqualini, R., and Ruoslahti, E. "Molecular heterogeneity of the vascular endothelium revealed by in vivo phage display." *J Clin Invest* 102:430-437 (1998).

Rajotte, D., and Ruoslahti, E. "Membrane dipeptidase is the receptor for a lung-targeting peptide identified by in vivo phage display." *J Biol Chem* 274:11593-11598 (1999).

Reed C C, Waterhouse A, Kirby S, Kay P, Owens R T, McQuillan D J, Iozzo R V. "Decorin prevents metastatic spreading of breast cancer." *Oncogene* 24:1104-10 (2005).

Reed C C, Iozzo R V: "The role of decorin in collagen fibrillogenesis and skin homeostasis." *Glycoconj. J* 19:249-255 (2002).

Rider C C. "Heparin/heparan sulphate binding in the TGF-β cytokine superfamily." *Biochem Soc Trans* 34:458-460 (2006).

Ruoslahti, E. "Specialization of tumour vasculature." *Nat Rev Cancer* 2:83-90 (2002).

Ruoslahti E, Yamaguchi Y. "Proteoglycans as modulators of growth factor activities." *Cell* 64: 867-9 (1991).

Santra M, Reed C C, Iozzo R V. "Decorin binds to a narrow region of the epidermal growth factor (EGF) receptor, partially overlapping but distinct from the EGF-binding epitope." *J Biol Chem* 277:35671-81 (2002).

Santra M, Eichstetter I, Iozzo R V: "An anti-oncogenic role for decorin. Down-regulation of ErbB2 leads to growth suppression and cytodifferentiation of mammary carcinoma cells." *J. Biol. Chem.* 275:35153-35161 (2000).

Santra M, Eichstetter 1, Iozzo R V. "An anti-oncogenic role for decorin. Down-regulation of ErbB2 leads to growth suppression and cytodifferentiation of mammary carcinoma cells." *J Biol Chem* 275:35153-61 (1999).

Seidler D G, et al. "Decorin protein core inhibits in vivo cancer growth and metabolism by hindering epidermal growth factor receptor function and triggering apoptosis via caspase-3 activation." *J Biol Chem* 281:26408-26418 (2006).

Shah M, Foreman D M, Ferguson M W. "Neutralisation of TGF-beta 1 and TGF-beta 2 or exogenous addition of TGF-beta 3 to cutaneous rat wounds reduces scarring." *J Cell Sci.* 108:985-1002 (1995).

Shipitsin M, et al. "Molecular definition of breast tumor heterogeneity." *Cancer Cell* 11, 259-273 (2007).

Singer A J, Clark R A F. "Cutaneous wound healing." *N Engl J Med* 341:738-746 (1999).

Sullivan M M, et al. "Matricellular hevin regulates decorin production and collagen assembly." *J Biol Chem* 281: 27621-27632 (2006).

Tralhao J G, Schaefer L, Micegova M, Evaristo C, Schonherr E, Kayal S, Veiga-Fernandes H, Danel C, Iozzo R V, Kresse H, Lemarchand P. "In vivo selective and distant killing of cancer cells using adenovirus-mediated decorin gene transfer." *FASEB J* 17:464-6 (2003).

Weis S M, et al. "A role for decorin in the remodeling of myocardial infarction." *Matrix Biol.* 24:313-324 (2005).

Werner S, Grose R: "Regulation of wound healing by growth factors and cytokines." *Physiol Rev* 83:835-870 (2003).

Yamaguchi Y, Mann D, Ruoslahti E. "Negative regulation of transforming growth factor-β by the proteoglycan decorin." *Nature* 346:281-284 (1990).

Yamaguchi Y, Ruoslahti E. "Expression of human proteoglycan in Chinese hamster ovary cells inhibits cell proliferation." *Nature* 336:244-246 (1988).

Yang L, Qiu C X, Ludlow A, Ferguson M W, Brunner G: "Active transforming growth factor-beta in wound repair: determination using a new assay." *Am. J. Pathol.* 154:105-111 (1999).

Zhang G, et al. "Decorin regulates assembly of collagen fibrils and acquisition of biomechanical properties during tendon development." *J. Cell Biochem.* 98:1436-1449 (2006).

Zorko M, Langel U. "Cell penetrating peptides: mechanism and kinetics of cargo delivery." *Adv. Drug Deliv Rev* 57:529-45 (2005).

Zurita et al *Cancer Res.* 64:435-9 (2004).

What is claimed is:

1. An isolated peptide comprising an amino acid segment comprising the amino acid sequence of SEQ ID NO: 1, the amino acid sequence of SEQ ID NO: 1 having one or two conservative amino acid substitutions, or the amino acid sequence of SEQ ID NO: 2 having three or more conservative amino acid substitutions.

2. The isolated peptide of claim 1, wherein the amino acid sequence of SEQ ID NO: 1 has two conservative amino acid substitutions, wherein the amino acid sequence of SEQ ID NO: 2 has three conservative amino acid substitutions.

3. An isolated peptide comprising an amino acid segment comprising the amino acid sequence of SEQ ID NO: 1, wherein the peptide has a length of less than 100 residues.

4. The isolated peptide of claim 1, wherein the peptide has a length of less than 50 residues.

5. The isolated peptide of claim 1, wherein the peptide has a length of less than 20 residues.

6. The isolated peptide of claim 1, wherein the amino acid segment is cyclic.

7. The isolated peptide of claim 6, wherein the amino acid segment is cyclicized via a disulfide bond.

8. The isolated peptide of claim 1, wherein the peptide selectively homes to regenerating tissue.

9. The isolated peptide of claim 8, wherein the regenerating tissue is at a site of injury.

10. The isolated peptide of claim 8, wherein the regenerating tissue is at a surgical site.

11. The isolated peptide of claim 1, wherein the peptide selectively homes to a tumor.

12. The isolated peptide of claim 1, wherein the peptide selectively homes to a site of inflammation.

13. The isolated peptide of claim 1, wherein the peptide selectively homes to a site of arthritis.

14. The isolated peptide of claim 1, wherein the peptide consists of the amino acid segment.

15. A conjugate, wherein the conjugate comprises a moiety linked to the peptide of claim 1.

16. The conjugate of claim 15, wherein the peptide selectively interacts with regenerating tissue.

17. The conjugate of claim 15, wherein the peptide selectively interacts with tissue at a site of inflammation.

18. The conjugate of claim 15, wherein the peptide selectively interacts with tissue at a site of arthritis.

19. The conjugate of claim 15, wherein the peptide selectively interacts with a tumor.

20. The conjugate of claim 15, wherein the moiety is a an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination.

21. The conjugate of claim 15, wherein the moiety is a therapeutic agent.

22. The conjugate of claim 21, wherein the therapeutic agent is decorin.

23. The conjugate of claim 15, wherein the moiety is a detectable agent.

24. The conjugate of claim 15, wherein the conjugate comprises a virus.

25. The conjugate of claim 24, wherein the conjugate comprises a phage.

26. An isolated peptide comprising an amino acid segment comprising the amino acid sequence of SEQ ID NO: 1 or SEQ ID NO: 2, or the amino acid sequence of SEQ ID NO: 1 or SEQ ID NO: 2 having one or more conservative amino acid substitutions, wherein the peptide is fused to at least one heterologous moiety, wherein the moiety is not a polypeptide.

27. An isolated peptide comprising an amino acid segment comprising the amino acid sequence of SEQ ID NO: 1 or SEQ ID NO: 2, or the amino acid sequence of SEQ ID NO: 1 or SEQ ID NO: 2 having one or more conservative amino acid substitutions, wherein the peptide is part of a chimeric protein.

28. An isolated peptide consisting of an amino acid segment, wherein the amino acid segment consists of the amino acid sequence of SEQ ID NO: 1 or SEQ ID NO: 2, or the amino acid sequence of SEQ ID NO: 1 or SEQ ID NO: 2 having one or more conservative amino acid substitutions, wherein the peptide has a length of less than 20 residues.

29. An isolated peptide consisting of an amino acid segment, wherein the amino acid segment consists of the amino acid sequence of SEQ ID NO:1 or SEQ ID NO:2.

30. An isolated peptide consisting of an amino acid segment consisting of the amino acid sequence of SEQ ID NO: 1 or SEQ ID NO: 2, or the amino acid sequence of SEQ ID NO: 1 or SEQ ID NO: 2 having one, two, or three conservative amino acid substitutions.

31. An isolated peptide comprising an amino acid segment comprising the amino acid sequence of SEQ ID NO: 2, or the amino acid sequence of SEQ ID NO: 2 having one or more conservative amino acid substitutions, wherein the peptide has a length of less than 20 residues.

32. The isolated peptide of claim 31, wherein the amino acid segment is cyclic.

33. The isolated peptide of claim 32, wherein the amino acid segment is cyclicized via a disulfide bond.

34. The isolated peptide of claim 31, wherein the peptide selectively homes to regenerating tissue.

35. The isolated peptide of claim 31, wherein the peptide selectively homes to a tumor.

36. The isolated peptide of claim 31, wherein the peptide selectively homes to a site of inflammation.

37. The isolated peptide of claim 31, wherein the peptide is part of a chimeric protein.

38. The isolated peptide of claim 31, wherein the peptide consists of the amino acid segment, wherein the amino acid segment consists of the amino acid sequence.

39. A conjugate, wherein the conjugate comprises a moiety linked to the peptide of claim 31.

40. An isolated peptide comprising an amino acid segment comprising the amino acid sequence of SEQ ID NO: 2, or the amino acid sequence of SEQ ID NO: 2 having one or more conservative amino acid substitutions, wherein the peptide has a length of less than 100 residues, wherein the amino acid segment is cyclic.

41. The isolated peptide of claim 40, wherein the amino acid segment is cyclicized via a disulfide bond.

42. The isolated peptide of claim 40, wherein the peptide selectively homes to regenerating tissue.

43. The isolated peptide of claim 40, wherein the peptide selectively homes to a tumor.

44. The isolated peptide of claim 40, wherein the peptide selectively homes to a site of inflammation.

45. The isolated peptide of claim 40, wherein the peptide is part of a chimeric protein.

46. The isolated peptide of claim 40, wherein the peptide consists of the amino acid segment, wherein the amino acid segment consists of the amino acid sequence.

47. A conjugate, wherein the conjugate comprises a moiety linked to the peptide of claim 40.

48. An isolated peptide comprising an amino acid segment comprising the amino acid sequence of SEQ ID NO: 2, or the amino acid sequence of SEQ ID NO: 2 having one or more conservative amino acid substitutions, wherein the peptide has a length of less than 100 residues, wherein the peptide is part of a chimeric protein.

49. The isolated peptide of claim 48, wherein the amino acid segment is cyclic.

50. The isolated peptide of claim 49, wherein the amino acid segment is cyclicized via a disulfide bond.

51. The isolated peptide of claim 48, wherein the peptide selectively homes to regenerating tissue.

52. The isolated peptide of claim 48, wherein the peptide selectively homes to a tumor.

53. The isolated peptide of claim 48, wherein the peptide selectively homes to a site of inflammation.

54. The isolated peptide of claim 48, wherein the peptide consists of the amino acid segment, wherein the amino acid segment consists of the amino acid sequence.

55. A conjugate, wherein the conjugate comprises a moiety linked to the peptide of claim 48.

56. A conjugate, wherein the conjugate comprises a moiety linked to a peptide comprising an amino acid segment comprising the amino acid sequence of SEQ ID NO: 2, or the amino acid sequence of SEQ ID NO: 2 having one or more conservative amino acid substitutions, wherein the peptide has a length of less than 100 residues.

57. The conjugate of claim 56, wherein the peptide selectively interacts with regenerating tissue.

58. The conjugate of claim 56, wherein the peptide selectively interacts with tissue at a site of inflammation.

59. The conjugate of claim 56, wherein the peptide selectively interacts with tissue at a site of arthritis.

60. The conjugate of claim 56, wherein the peptide selectively interacts with a tumor.

61. The conjugate of claim 56, wherein the moiety is a an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, a fluorophore, fluorescein, rhodamine, a radionuclide, indium-111, technetium-99, carbon-11, carbon-13, or a combination.

62. The conjugate of claim 56, wherein the moiety is a therapeutic agent.

63. The conjugate of claim 62, wherein the therapeutic agent is decorin.

64. The conjugate of claim 56, wherein the moiety is a detectable agent.

65. The conjugate of claim 56, wherein the conjugate comprises a virus.

66. The conjugate of claim 65, wherein the conjugate comprises a phage.

67. The isolated peptide of claim 1, wherein the peptide has a length of less than 100 residues.

68. The isolated peptide of claim 1, wherein the amino acid sequence of SEQ ID NO: 1 has one conservative amino acid substitution.

69. An isolated peptide comprising an amino acid segment comprising the amino acid sequence of SEQ ID NO: 1.

70. An isolated peptide comprising an amino acid segment comprising the amino acid sequence of SEQ ID NO: 2, wherein the peptide has a length of less than 70 residues.

71. An isolated peptide comprising an amino acid segment comprising the amino acid sequence of SEQ ID NO: 1 or the amino acid sequence of SEQ ID NO: 1 having one or more conservative amino acid substitutions, wherein the peptide has a length of less than 50 residues.

72. An isolated peptide comprising an amino acid segment comprising the amino acid sequence of SEQ ID NO: 2 or the amino acid sequence of SEQ ID NO: 2 having one or more conservative amino acid substitutions, wherein the peptide has a length of less than 30 residues.

73. An isolated peptide comprising an amino acid segment comprising the amino acid sequence of SEQ ID NO: 1 having four or more conservative amino acid substitutions, wherein the peptide has a length of less than 100 residues.

74. An isolated peptide comprising an amino acid segment comprising the amino acid sequence of SEQ ID NO: 2 having two or more conservative amino acid substitutions, wherein the peptide has a length of less than 90 residues.

* * * * *

```
                        SEQUENCE LISTING

<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

Cys Ala Arg Ser Lys Asn Lys Asp Cys
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Cys Arg Lys Asp Lys Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Arg Ala Arg Lys Lys Asn Lys Asn Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Cys Ala Arg Ser Thr Lys Ala Thr Cys
```

-continued

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Cys Ala Arg Ser Lys Asn Lys Asp Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Cys Ala Gln Ser Asn Asn Lys Asp Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Cys Arg Lys Asp Lys Cys
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Cys Arg Ala Ser Lys Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Lys Ala Arg Glu Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence; note =
      synthetic construct
```

```
<220> FEATURE:
<221> NAME/KEY: VARIANT
<222> LOCATION: 1, 4, 6
<223> OTHER INFORMATION: Xaa = Any Amino Acid

<400> SEQUENCE: 10

Xaa Asx Asx Xaa Asx Xaa
 1               5

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11
acgtggatcc atgaaggcca ctatcatcct ccttc                                 35

<210> SEQ ID NO 12
<211> LENGTH: 98
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12
atccgctcga gttagtgatg gtgatggtga tgcgagctgc cgcgcggcac caggtcgacg      60
aattccgagc ccttatagtt tccgagttga atggcaga                             98

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 13
aattttgtgc acgttcgaag aacaaagatt gcg                                  33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 14
tcgacgcaat ctttgttctt cgaacgtgca caa                                  33

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 15
aattttgccg gaaggataag tgcg                                            24

<210> SEQ ID NO 16
<211> LENGTH: 24
```

```
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 16
tcgacgcact tatccttccg gcaa                                              24

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 17
acgtggatcc ggaccgtttc aacagagagg cttatttgac tttatgctag a                51

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 18
atccgctcga gttagtgatg gtgatggtga tgcgagct                               38

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Lys Leu Ala Lys Leu Ala Lys Lys Leu Ala Lys Leu Ala Lys Lys Leu
 1               5                  10                  15

Ala Lys Lys Leu Ala Lys Ala Ala Lys Lys Ala Ala
            20                  25

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20

Lys Leu Gly Lys Lys Leu Gly
 1               5
```